United States Patent
Jasti et al.

(10) Patent No.: US 9,090,473 B2
(45) Date of Patent: Jul. 28, 2015

(54) [N]CYCLOPARAPHENYLENES (CCP), [N]MACROCYCLE INTERMEDIATES AND METHODS OF MAKING SAME

(71) Applicant: TRUSTEES OF BOSTON UNIVERSITY, Boston, MA (US)

(72) Inventors: Ramesh Jasti, Somerville, MA (US); Jianlong Xia, New York, NY (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 14/352,508

(22) PCT Filed: Jan. 23, 2013

(86) PCT No.: PCT/US2013/022608
§ 371 (c)(1),
(2) Date: Apr. 17, 2014

(87) PCT Pub. No.: WO2013/112493
PCT Pub. Date: Aug. 1, 2013

(65) Prior Publication Data
US 2014/0308195 A1    Oct. 16, 2014

Related U.S. Application Data

(60) Provisional application No. 61/589,739, filed on Jan. 23, 2012.

(51) Int. Cl.
| | | |
|---|---|---|
| C07C 15/14 | (2006.01) | |
| C01B 31/02 | (2006.01) | |
| C07C 43/21 | (2006.01) | |
| C07C 23/18 | (2006.01) | |
| C07C 41/30 | (2006.01) | |
| C07C 50/30 | (2006.01) | |
| C07F 7/18 | (2006.01) | |
| B82Y 30/00 | (2011.01) | |

(52) U.S. Cl.
CPC ............. *C01B 31/022* (2013.01); *C07C 15/14* (2013.01); *C07C 23/18* (2013.01); *C07C 41/30* (2013.01); *C07C 43/21* (2013.01); *C07C 50/30* (2013.01); *C07F 7/1892* (2013.01); *B82Y 30/00* (2013.01); *C07C 2103/93* (2013.01); *Y10S 977/742* (2013.01)

(58) Field of Classification Search
CPC ........................... C01B 31/022; Y10S 977/75
See application file for complete search history.

(56) References Cited

U.S. PATENT DOCUMENTS

2011/0166390 A1    7/2011    Jasti et al.

OTHER PUBLICATIONS

Gavezotti, Accounts of Chemical Research, Are Crystal structures Predictable?, 1994, 27 pp. 309-314.*
Jagadeesh et al. "The Interplay of Angle Strain and Aromaticity: Molecular and Electronic Structures of [On] Paracylophanes." J. Mol. Model, 2000, vol. 6, pp. 226-233.
Jasti et al. "Sythesis, Characterization, and Theory of [9]-, [12]-, and [18]Cycloparaphenylene: Carbon Nanohoop Structures." J. Am. Chem. Soc., 2008, vol. 130, pp. 17646-17647.
Sisto et al. "Selective Synthesis of Strained [7]Cycloparaphenylene: An Orange-Emitting Fluorophore." J. Am. Chem. Soc., 2011, vol. 133, pp. 15800-15802.
Segawa et al. "Concise Syntheses and Crystal Structure of [12]Cycloparaphenylene." Angew. Chem. Int., Ed. 2011, vol. 50, pp. 3244-3248.
Iwamoto et al. "Selective and Random Synthesis of [n]Cycloparaphenylenes (n=813) and Size Dependence of Their Electronic Properties." J. Am. Chem. Soc., 2011, vol. 133, pp. 8354-8361.

* cited by examiner

*Primary Examiner* — Paul A Zucker
(74) *Attorney, Agent, or Firm* — Nixon Peabody LLP

(57) ABSTRACT

The present invention provides the compound [6]-cycloparaphenylene, cycloparaphenylene intermediates (e.g. [n]macrocycles), and methods for making [n]cycloparaphenylenes and [n]cycloparaphenylene intermediates in quantities not previously available. The cycloparaphenylene compounds and their intermediates can be useful in nanotube preparation and in the preparation of other supramolecular structures.

7 Claims, 7 Drawing Sheets side view top-down view

[N]CYCLOPARAPHENYLENES (CCP), [N]MACROCYCLE INTERMEDIATES AND METHODS OF MAKING SAME

CROSS-REFERENCE TO RELATED APPLICATIONS

This application is a 35 U.S.C. §371 National Phase Entry Application of International Application No. PCT/US2013/022608 filed Jan. 23, 2013, which designates the U.S., and which claims benefit under 35 U.S.C. §119(e) of the U.S. Provisional Application No. 61/589,739, filed Jan. 23, 2012, the content of which is incorporated herein by reference in its entirety for all purposes.

BRIEF DESCRIPTION OF DRAWINGS

The skilled artisan will understand that the drawings, described below, are for illustration purposes only. The drawings are not intended to limit the scope of the present teaching in any way.

DESCRIPTION

Figure 1:
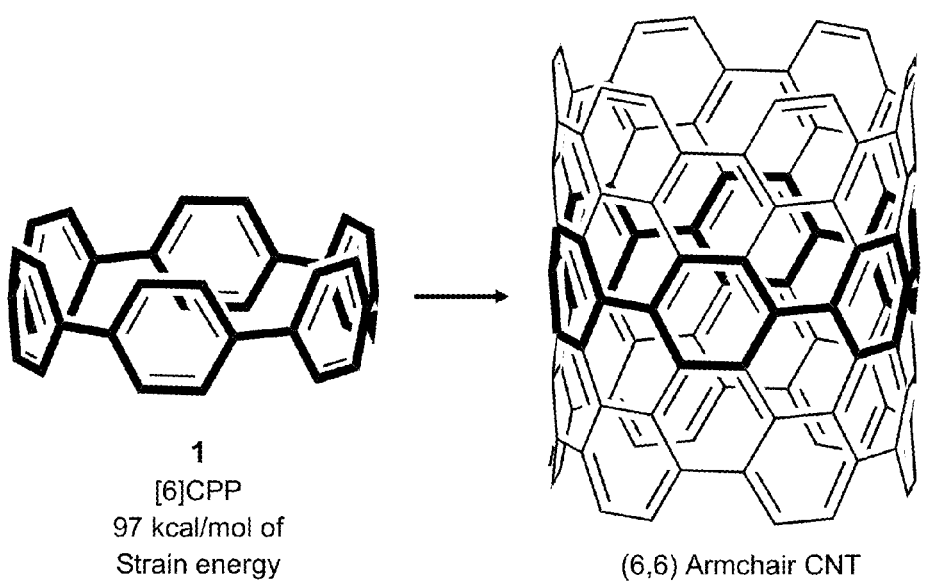
FIG. 1 is an illustration of [6]CPP which is a possible precursor to the (6,6) armchair nanotube that is also shown.

All literature and similar materials cited in this application, including but not limited to patents, patent applications, articles, books and treatises, regardless of the format of such literature or similar material, are expressly incorporated by reference herein in their entirety for any and all purposes.
Field The present invention pertains to the field of conjugated macrocycles including the synthesis of cycloparaphenylenes (CPPs) of various sizes, their related intermediates and nanostructures formed therefrom.
Introduction Hoop-shaped conjugated macrocycles are of interest due to the potential commercial applications of their electronic, thermal, optical, and supramolecular properties. For example, macrocycles feature size-dependent optoelectronic properties, as well as nano-sized cavities that could be useful in supramolecular chemistry. One class of hoop-shaped conjugated macrocycles is cycloparaphenylenes (CPPs), in which 1,4-connected phenyl rings form nano-sized macrocycles.

Carbon nanotubes (CNTs) are very small tube-shaped structures that may be composed of a graphene sheet connected to itself along the long edge. Carbon nanotubes exhibit extremely high electrical and thermal conductivity, very small diameters (much less than 100 nm), and large aspect ratios (i.e., length to diameter ratios greater than 100). These features make CNTs useful components for electron field emitters, white light sources, lithium secondary batteries, hydrogen storage cells, transistors, and cathode ray tubes.

Despite the great potential of CCPs in materials science, nanotechnology, and nanotube synthesis, CPPs have yet to be widely explored in many applications, at least partially due to limitations on available synthetic methodologies as well as costs related thereto. To date, no single method is able to selectively and economically produce CPPs in a range of different sizes.

DEFINITIONS

For the purposes of interpreting this specification, the following definitions will apply and whenever appropriate, terms used in the singular will also include the plural and vice versa. In the event that any definition set forth below conflicts with the usage of that word in any other document, the definition set forth below shall always control for purposes of interpreting the scope and intent of this specification and its associated claims. Notwithstanding the foregoing, the scope and meaning of any document incorporated herein by reference should not be altered by the definition presented below. Rather, said incorporated document should be interpreted as it would be by the ordinary practitioner based on its content and disclosure with reference to the content of the description provided herein.

The use of "or" means "and/or" unless stated otherwise or where the use of "and/or" is clearly inappropriate. The use of "a" means "one or more" unless stated otherwise or where the use of "one or more" is clearly inappropriate. The use of "comprise," "comprises," "comprising" "include," "includes," and "including" are interchangeable and not intended to be limiting. Furthermore, where the description of one or more embodiments uses the term "comprising," those skilled in the art would understand that in some specific instances, the embodiment or embodiments can be alternatively described using language "consisting essentially of" and/or "consisting of."

As used herein, the abbreviations for any protective groups, amino acids, and other compounds are, unless indicated otherwise, in accord with their common usage, recognized abbreviations, or the IUPAC-IUB Commission on Biochemical Nomenclature, Biochem., 11:942-944 (1972).

"Acyl" refers to a group of formula LA-C(O)—, wherein LA is lower alkyl as defined below. Exemplary acyl groups also include acetyl, propanoyl, 2-methylpropanoyl, butanoyl and palmitoyl.

"Alkenyl" refers to an alkyl group comprising at least one carbon-carbon double bond. The alkenyl group can optionally comprise one or more "alkyl group substituents." Exemplary alkenyl groups include vinyl, allyl, n-pentenyl, decenyl, dodecenyl, tetradecadienyl, heptadec-8-en-1-yl and heptadec-8,11-dien-1-yl.

"Alkoxy" refers to a LA-O— group, wherein LA is lower alkyl as defined below. Exemplary alkoxy groups include methoxy, ethoxy, n-propoxy, i-propoxy, n-butoxy, and heptoxy.

"Alkyl" refers to an aliphatic hydrocarbon group which can be straight chain or branched comprising from 1 to about 50 carbon atoms, and in some embodiments from about 1 to about 30 carbon atoms. "Lower alkyl" refers to an alkyl group comprising from 1 to about 8 carbon atoms; in some embodiments from 1 to about 6 carbon atoms and in some embodiments from 1 to about 4 carbon atoms. Some exemplary lower alkyl groups include methyl, ethyl, propyl, isopropyl, butyl, tert-butyl, sec-butyl, and isobutyl groups. "Higher alkyl" refers to an alkyl group comprising from about 8 to about 20 carbon atoms; in some embodiments from 9 to about 30 carbon atoms and in some embodiments from 9 to about 50 carbon atoms. The alkyl group can be optionally substituted with one or more alkyl group substituents which can be the same or different, where "alkyl group substituent" includes halide, amino, aryl, hydroxy, alkoxy, aryloxy, alkyloxy, alkylthio, arylthio, aralkyloxy, aralkylthio, carboxy, alkoxycarbonyl, oxo and cycloalkyl substituents. There can be optionally inserted along the alkyl chain one or more oxygen, silicon, sulfur, or substituted or unsubstituted nitrogen atoms, wherein the nitrogen substituent is lower alkyl. "Branched" refers to an alkyl group in which a lower alkyl group, such as methyl, ethyl or propyl, is attached to a linear alkyl chain. Exemplary alkyl groups include methyl, ethyl, i-propyl, n-butyl, t-butyl, n-pentyl, heptyl, octyl, decyl, dodecyl, tridecyl, tetradecyl, pentadecyl and hexadecyl.

An "alkylating agent" refers to a chemical species containing a lower alkyl, alkylene, cycloalkyl, heterocycloalkyl, aryl, or heteroaryl group that donates its lower alkyl, alkylene, cycloalkyl, heterocycloalkyl, aryl, or heteroaryl group readily to other molecules. Exemplary alkylating agents include alkyl halides such as methyl iodide or the Grignard reagent. Other non-liming examples of alkylating agents and associated methods for alkylation of hydroxyl group are discussed in Michael B. Smith and Jerry March, *March's Advanced Organic Chemistry* (6th ed. 2007) at pages 587-656, 912-913 and 980-984 (and references discussed/referred to therein).

"Alkylene" refers to a straight or branched bivalent aliphatic hydrocarbon group having from 1 to about 20 carbon atoms. The alkylene group can be straight, branched, or cyclic. The alkylene group can be also optionally unsaturated and/or substituted with one or more "alkyl group substituents." There can be optionally inserted along the alkylene group one or more oxygen, sulfur or substituted or unsubstituted nitrogen atoms, wherein the nitrogen substituent is alkyl as previously described. Exemplary alkylene groups include methylene (—CH$_2$—), ethylene (—CH$_2$—CH$_2$—), propylene (—(CH$_2$)$_3$—), cyclohexylene (—C$_6$H$_{10}$—), —CH═CH—CH═CH— and —CH═CH—CH$_2$—.

"Alkylthio" refers to a LA-S— group, wherein LA is lower alkyl as previously defined. Exemplary alkylthio groups include methylthio, ethylthio, i-propylthio and heptylthio.

"Alkynyl" refers to an alkyl group comprising at least one carbon-carbon triple bond. The alkynyl group can optionally comprise one or more "alkyl group substituents." Exemplary alkynyl groups include ethynyl, propargyl, n-pentynyl, decynyl and dodecynyl.

"Aralkyl" refers to an Ar-LA- group, wherein Ar is aryl as defined below and LA is lower alkyl as previously defined. Exemplary aralkyl groups include benzyl, phenylethyl and naphthylmethyl.

"Aralkyloxy" refers to an ARA-O— group, wherein ARA is the aralkyl group is as previously defined. An exemplary aralkyloxy group is benzyloxy.

"Aralkylthio" refers to an ARA-S— group, wherein ARA is the aralkyl group is as previously defined. An exemplary aralkylthio group is benzylthio.

"Aroyl" means an Ar—C(O)— group, wherein Ar is aryl as defined below. Exemplary aroyl groups include benzoyl and 1- and 2-naphthoyl.

"Aryl" refers to an aromatic carbocyclic radical containing about 5 to about 10 carbon atoms. The aryl group can be optionally substituted with one or more substituents, which can be the same or different, where "aryl group substituent" includes lower alkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acyloxy, acylamino, aroylamino, carbamoyl, alkylcarbamoyl, dialkylcarbamoyl, arylthio, alkylthio, alkylene and —NR$^7$R$^8$, where R$^7$ and R$^8$ are each independently hydrogen, lower alkyl, aryl and aralkyl. Exemplary aryl groups include substituted or unsubstituted phenyl and substituted or unsubstituted naphthyl.

"Aryloxy" refers to an Ar—O— group, wherein Ar is the aryl group as previously defined. Exemplary aryloxy groups include phenoxy and naphthoxy.

"Arylthio" refers to an Ar—S— group, wherein Ar is the aryl group as previously defined. Exemplary arylthio groups include phenylthio and naphthylthio.

"Aspect ratio" refers to the length divided by diameter of the individual nanostructure. For example, a nanotube having a length of 30,000 nanometers (30 µm) and a diameter of 50 nanometers would have an aspect ratio of 600 (30,000/50=600).

"Boronate" refers to esters of boronic acid. Boronates include compounds of the following general formula:

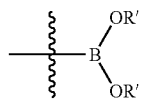

wherein the bond with the squiggly line represents the bond that links the boronate to the compound of interest and each R' is alkyl, alkylene, cycloalkyl, heterocycloalkyl, aryl, or heteroaryl. Alternatively, the two R' groups can be combined with the atoms to which each is attached form a heterocycloalkyl group. An exemplary boronate is isopropyl pinacol boronate (Bpin), of the formula:

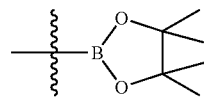 [SMILES: *B1OC(C)(C)C(C)(C)O1]

wherein the bond with the squiggly line represents the bond that links the boronate to the compound of interest.

"Contacting" refers to the process whereby at least two reagent molecules (which may be the same molecule as in, for example, polymerization reactions) interact with each other in a manner that permits them to undergo a chemical reaction to form a product. One of ordinary skill in the art will appreciate that, in some embodiments, the reaction product can be produced directly from a reaction between said two or more reagent molecules or otherwise be produced by transition through one or more intermediates, whereby additional reactive species may, or may not (depending on the circumstances) be required to generate the intended product.

"Cycloalkyl" refers to a non-aromatic mono- or multicyclic ring system of about 3 to about 10 carbon atoms. The cycloalkyl group can be optionally partially unsaturated. The cycloalkyl group can be also optionally substituted with an aryl group, oxo and/or alkylene substituent. Representative monocyclic cycloalkyl rings include cyclopentyl, cyclohexyl and cycloheptyl. Useful multicyclic cycloalkyl rings include adamantyl, octahydronaphthyl, decalin, camphor, camphane, and noradamantyl.

"Dialkylamino" refers to an $R^9R^{10}N$— group, wherein each of $R^9$ and $R^{10}$ is independently a lower alkyl group as previously defined. Exemplary alkylamino groups include ethylmethylamino, dimethylamino, and diethylamino.

"Halo" or "halide" refers to fluorine (F), chlorine (Cl), bromine (Br), or iodine (I).

"Heteroaryl" refers to a monocyclic or fused bicyclic or tricyclic aromatic ring assembly containing 5 to about 20 ring atoms, where from 1 to 4 of the ring atoms can be a heteroatom such as N, O or S. Exemplary heteroaryls include pyridyl, indolyl, indazolyl, quinoxalinyl, quinolinyl, isoquinolinyl, benzothienyl, thienyl or any other radicals substituted, especially mono- or di-substituted, by, for example, alkyl, nitro or halogen.

"Heterocycloalkyl" refers to a ring system having from 3 ring atoms to about 20 ring atoms and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. Exemplary heterocycloalkyls include tetrahydrofuranyl, imidazolidinyl, piperazinyl, indolinyl and quinuclidinyl.

The "length of a nanotube" refers to the length along the dimension perpendicular to the plane of the nanotube's diameter. For example, in a (6,6) armchair carbon nanotube:

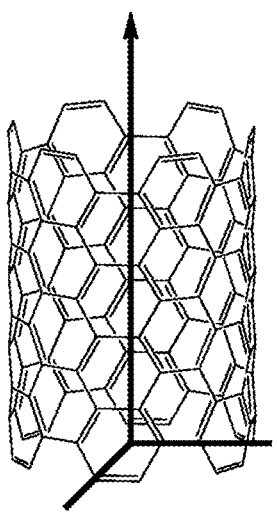

the length dimension is represented by the bold arrow.

"Nanopore" refers to a nanometer scale in diameter hole in a substrate.

"Nanotube" refers to a nanometer-scale tube-like structure.

"Palladium catalyst" refers to a complex of palladium (in any oxidation state) and various ligands known in the art. Exemplary palladium catalysts include tetrakis(triphenylphosphine)palladium(0), bis(triphenylphosphine)palladium(II) dichloride, tris(dibenzylideneacetone)dipalladium (0), and palladium(II) acetate.

A "protecting group" refers to a compound or a chemical moiety that prevents a functional group within a molecule from reacting until the protecting group is removed. Various protecting groups are well known in the art and include, but are not limited to, Acetyl, Benzoyl, Benzyl, β-Methoxyethoxymethyl ether, bis-(4-methoxyphenyl)phenylmethyl (DMT), Methoxymethyl ether (MOM), Methoxytrityl (MMT), p-Methoxybenzyl ether (PMB), Methylthiomethyl ether, Pivaloyl, silyl ethers, Tetrahydropyranyl (THP), Trityl, methyl ethers, ethoxy ethers, Carbobenzyloxy, 3,4-Dimethoxybenzyl (DMPM), p-methoxyphenyl (PMP), Tosyl (Ts), Sulfonamides, and Dithianes. Other non-liming examples of protecting groups are discussed in Theodora W. Green & Peter G. M. Wuts, *Greene's Protective Groups in Organic Synthesis* (4th ed. 2007).

"Silyl ethers" are a class of protecting groups that contain a silicon atom covalently bonded to an alkoxy group. Various silyl ethers are well known in the art and include, but are not limited to, trimethylsilyl (TMS), tert-butyldiphenylsilyl (TBDPS), tert-butyldimethylsilyl (TBS/TBDMS) and triisopropylsilyl (TIPS). Silyl ethers can be used to protect phenolic oxygen moieties (i.e. a phenol group).

"S-Phos" is 2-Dicyclohexylphosphino-2',6'-dimethoxybiphenyl:

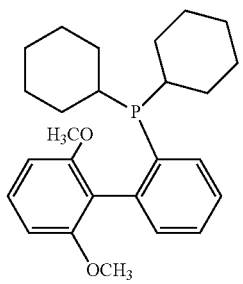 [SMILES: COc1cccc(OC)c1-c1ccccc1P(C1CCCCC1)C1CCCCC1]

General

It is to be understood that the discussion set forth below in this "General" section can pertain to some, or to all, of the various embodiments of the invention described herein.

Potential applications of macrocycles in general and CPPs in particular include dyes, drug delivery and gas storage. Other possible applications include battery and capacitor materials, materials for field effect transistors, light emitting materials and materials for organic photovoltaics.

Cycloparaphenylenes are the smallest structural unit of armchair carbon nanotubes (CNTs). Thus, methods that permit the increased availability of CPPs may eventually lead to new synthetic methods for producing CNTs.

The present invention describes new methods of producing CPPs which dramatically lowers their cost. It also describes an as-yet-unsynthesized CCP, [6]cycloparaphenylene, the smallest CPP synthesized to date.

Palladium Catalysts

Palladium catalysts useful in the practice of methods of this invention are those that are suitable for catalyzing the Suzuki-Miyaura reaction. Exemplary catalysts are discussed in Stephen L. Buchwald et al., *Catalysts for Suzuki-Miyaura Coupling Processes: Scope and Studies of the Effect of Ligand Structure*, 127 J. AM. CHEM. SOC. 4685 (2005), including in the references therein, all of which are hereby incorporated by reference.

Phenol and Thiophenol Groups

The phenol or thiophenol groups of various compounds disclosed herein can be protected in various ways. The phenol or thiophenol group can be protected, for example as an ester, an ether or silyl ether. Exemplary methods and reagents suitable for protecting and deprotecting the phenol or thiophenol group are known in the art and can also be found in Theodora W. Green & Peter G. M. Wuts, *Greene's Protective Groups in Organic Synthesis* (4th ed. 2007) at pages 370-419 and references discussed/referred to therein. Those of skill in the art will appreciate that, depending on the exact nature of the protecting group, a phenol or thiophenol protecting group can be acid labile, base labile, fluoride labile or photochemically labile, all of which are within the scope of disclosed embodiments of this invention.

Various Embodiments of the Invention

It should be understood that the order of steps or order for performing certain actions is immaterial so long as the present teachings remain operable or unless otherwise specified. Moreover, in some embodiments, two or more steps or actions can be conducted simultaneously so long as the present teachings remain operable or unless otherwise specified.

Compounds

A. Formula I

The present invention provides the first ever synthesis of [6]cycloparaphenylene ([6]CPP). [6]cycloparaphenylene is useful for the preparation of armchair nanotubes and other supramolecular structures. Although U.S. Ser. No. 12/955,211 suggests that [6]cycloparaphenylene can be produced by the method disclosed therein, subsequent literature publications have shown that [6]cycloparaphenylene indeed cannot be made using existing procedures (See for Example Sisto et al. J. Am. Chem. Soc. 2011, 133, 15800-15802). Thus, in some embodiments, this invention pertains to [6]CCPs that have the formula I:

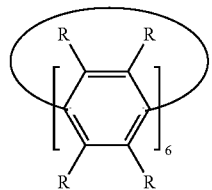

(I)

In formula I, each R can independently be hydrogen, lower alkyl, alkylene, cycloalkyl, heterocycloalkyl, aryl or heteroaryl or independently two R groups on adjacent carbons can be combined with the atoms to which each is attached to form a 4, 5, or 6 membered cycloalkyl, heterocycloalkyl, aryl or heteroaryl ring. An exemplary method for the synthesis of [6]CCPs can be found in Examples 1-6 and FIG. 2, wherein the R groups in the final products will depend on the moieties attached to the 6-membered rings of the starting materials.

In some embodiments, each R group in formula I is hydrogen. In some embodiments, each R group in formula I can be methyl. In some embodiments, each R group in formula I can be ethyl. In some embodiments, each R group in formula I can be independently hydrogen, methyl or ethyl. In some embodiments, each R group in formula I can be independently hydrogen, methyl, ethyl, propyl, isopropyl, butyl, tert-butyl, sec-butyl or isobutyl. In some embodiments, each R group in formula I is independently lower alkyl, cycloalkyl or aryl. In some embodiments, each R in formula I can be independently lower alkyl, cycloalkyl or aryl. In some embodiments, each R in formula I can be independently lower alkyl or aryl. In some embodiments, each R in formula I can be lower alkyl. In some embodiments, each R in formula I can independently be lower alkyl or cycloalkyl. In some embodiments, each R in formula I can be alkylene. In some embodiments, each R in formula I can be cycloalkyl. In some embodiments, each R in formula I can be heterocycloalkyl. In some embodiments, each R in formula I can be heteroaryl.

In some embodiments, the [6]CPP is substantially pure, where substantially pure means [6]CPP is greater than 90% mol fraction of a mixture, preferably greater than 95% mol fraction of a mixture, and even more preferably greater than 99% mol fraction of a mixture.

The ring closing step that produces the [6]macrocycle (compound 9) is an advancement that facilitates synthesis of the [6]CPP. The low yield shown for the product of Example 5 (12%) illustrates how energetically disfavored it is to close a ring of this size. Larger rings are more easily closed (See Reference 12 at 15801).

In some embodiments, two R groups on adjacent carbons that combine with atoms to which each is attached form a 5 or 6 membered cycloalkyl ring, the compound having the formula XX:

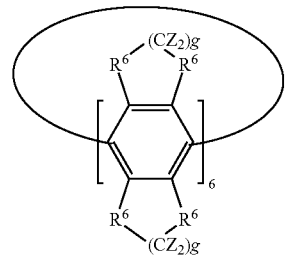

(XX)

wherein, each g is independently 0, 1 or 2, provided that: (i) at least one g is greater than 0; and (ii) if a g is 0, then each $R^6$ is $CZ_3$ such that no cycloalkyl ring is formed at that position, otherwise each $R^6$ is $CZ_2$, and each Z is independently hydrogen, F, Cl, Br or I.

B. Formula II

In some embodiments, the present invention is also directed to compounds of formula II.

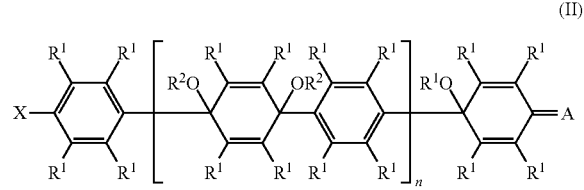

(II)

An example of a compound of formula II is compound 7. Compound 7 is itself useful in some embodiments of this invention because it is analogous to compound 3 in that it comprises the same terminal reactive groups but is two ring units longer. Indeed, compound 7 is produced from compound 3 (See: Examples 1-3). Accordingly, in some embodiments, this invention pertains to methods that can be used to produce intermediates of various lengths that themselves can be used to produce the [n]macrocycles and their corresponding [n]cycloparaphenylenes as further described herein.

In formula II, subscript n can be 1, 2, 3, 4, 5, 6, 7, 8, 9 or 10; A can be sulfur or oxygen; X can be F, Cl, Br or I; each $R^1$ can independently be hydrogen, lower alkyl, alkylene, cycloalkyl, heterocycloalkyl, aryl and heteroaryl or independently two $R^1$ groups on adjacent carbons can be combined with atoms to which each is attached to form a 4, 5 or 6 membered cycloalkyl, heterocycloalkyl, aryl or heteroaryl ring; and each $R^2$ can independently be lower alkyl, alkylene, cycloalkyl, heterocycloalkyl, aryl or heteroaryl.

In some embodiments, A is oxygen (O). In some embodiments A is sulfur (S).

In some embodiments, X is bromine. In some embodiments, X is chlorine. In some embodiments, X is iodine. In some embodiments, X is fluorine.

In some embodiments, subscript n is from 1 to about 5. In some embodiments, subscript n is from 1 to about 10, from 1 to about 6 or from 1 to about 3.

In some embodiments, each $R^2$ in formula II can independently be methyl or ethyl. In some embodiments, each $R^2$ in formula II can independently be lower alkyl or aryl. In some embodiments, each $R^2$ in formula II can be lower alkyl. In some embodiments, each $R^2$ in formula II can independently be lower alkyl or cycloalkyl. In some embodiments, each $R^2$ in formula II can be alkylene. In some embodiments, each $R^2$ in formula II can be cycloalkyl. In some embodiments, each $R^2$ in formula II can be heterocycloalkyl. In some embodiments, each $R^2$ in formula II can be heteroaryl.

In some embodiments, each $R^1$ in formula II can be hydrogen, methyl or ethyl. In some embodiments, each $R^1$ in formula II can be hydrogen. In some embodiments, each $R^1$ in formula II can be methyl. In some embodiments, each $R^1$ in formula II can be ethyl. In some embodiments, each $R^1$ in formula II can be independently hydrogen, methyl or ethyl. In some embodiments, each $R^1$ in formula II can be independently hydrogen, methyl, ethyl, propyl, isopropyl, butyl, tert-butyl, sec-butyl or isobutyl. In some embodiments, each $R^1$ in formula II can be independently lower alkyl, cycloalkyl or aryl. In some embodiments, each $R^1$ in formula II can be independently lower alkyl or aryl. In some embodiments, each $R^1$ formula II can be lower alkyl. In some embodiments, each $R^1$ in formula II can independently be lower alkyl or cycloalkyl. In some embodiments, each $R^1$ in formula II can be alkylene. In some embodiments, each $R^1$ in formula II can be cycloalkyl. In some embodiments, each $R^1$ in formula II can be heterocycloalkyl. In some embodiments, each $R^1$ in formula II can be heteroaryl.

In some embodiments, two $R^1$ in formula II groups on adjacent carbons that combine with atoms to which each is attached form a 5 or 6 membered cycloalkyl ring, wherein said 5 or 6 membered ring is has the formula XXI:

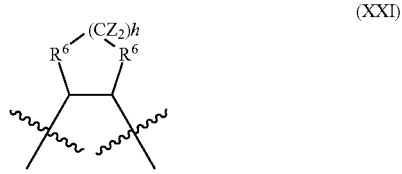

(XXI)

wherein, each $R^6$ is $CZ_2$; each Z is independently hydrogen, F, Cl, Br or I; and each h is independently 1 or 2.

In some embodiments, the compound of formula II is substantially pure, where substantially pure means the compound is greater than 90% mol fraction of the sample. In some embodiments, the compound of formula II is greater than 95% mol fraction of a sample, preferably greater than 99% mol fraction of the sample.

C. Formula XI

In some embodiments, this invention pertains to compounds of formula XI:

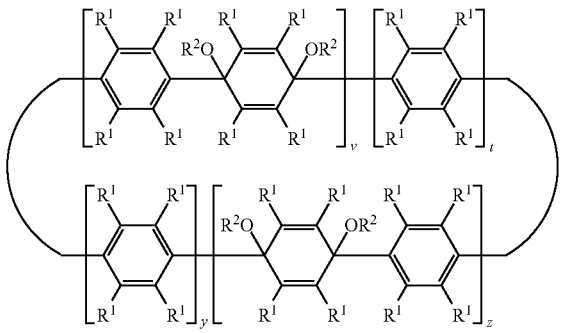

(XI)

In formula XI, t can be an integer from 1-3; v can be an integer from 0-12; y can be an integer from 1-3; and z can be an integer from 0-12; provided that; (i) v and z cannot both be zero; (ii) if v=0, then y+2z is greater than or equal to 5; and (iii) if z=0, then t+2v is greater than or equal to 5. In formula XI, each $R^1$ can independently be hydrogen, lower alkyl, alkylene, cycloalkyl, heterocycloalkyl, aryl or heteroaryl or independently two $R^1$ groups on adjacent carbons can be combined with atoms to which each is attached to form a 4,5 or 6 membered cycloalkyl, heterocycloalkyl, aryl or heteroaryl ring; and each $R^2$ can independently be lower alkyl, alkylene, cycloalkyl, heterocycloalkyl, aryl or heteroaryl.

In some embodiments, v, t, y, and z can be 1. In some embodiments, $R^1$ can be hydrogen methyl or ethyl. In some embodiments, $R^2$ can be methyl or ethyl. In other embodiments, t is 1; v is 2; y is 1; and z can be 0. In yet other embodiments, t can be 1; v can be 2; y can be 1; and z can be 1. In some embodiments, t can be 1; v can be 2; y can be 1; and z can be 2.

In some embodiments, each $R^2$ in formula XI can independently be lower alkyl or aryl. In some embodiments, each $R^2$ in formula XI can be lower alkyl. In some embodiments, each $R^2$ in formula XI can independently be lower alkyl or cycloalkyl. In some embodiments, each $R^2$ in formula XI can be alkylene. In some embodiments, each $R^2$ in formula XI can be cycloalkyl. In some embodiments, each $R^2$ in formula XI can be heterocycloalkyl. In some embodiments, each $R^2$ in formula XI can be heteroaryl.

In some embodiments, each $R^1$ in formula XI can be hydrogen. In some embodiments, each $R^1$ in formula XI can be methyl. In some embodiments, each $R^1$ in formula XI can be ethyl. In some embodiments, each $R^1$ in formula XI can be independently hydrogen, methyl or ethyl. In some embodiments, each $R^1$ in formula XI can be independently hydrogen, methyl, ethyl, propyl, isopropyl, butyl, tert-butyl, sec-butyl or isobutyl. In some embodiments, each $R^1$ in formula XI can be independently lower alkyl, cycloalkyl or aryl. In some embodiments, each $R^1$ can be independently lower alkyl or aryl. In some embodiments, each $R^1$ in formula XI can be lower alkyl. In some embodiments, each $R^1$ in formula XI can independently be lower alkyl or cycloalkyl. In some embodiments, each $R^1$ in formula XI can be alkylene. In some embodiments, each $R^1$ in formula XI can be cycloalkyl. In some embodiments, each $R^1$ in formula XI can be heterocycloalkyl. In some embodiments, each $R^1$ in formula XI can be heteroaryl.

In some embodiments, two $R^1$ groups on adjacent carbons that combine with atoms to which each is attached form a 5 or 6 membered cycloalkyl ring, wherein said 5 or 6 membered ring is has the formula XXI:

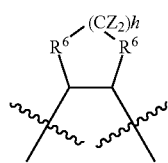

(XXI)

wherein, each $R^6$ is $CZ_2$; each Z is independently hydrogen, F, Cl, Br or I; and each h is independently 1 or 2.

In some embodiments, the compound of formula XI is substantially pure, where substantially pure means the compound is greater than 90% mol fraction of the sample. In some embodiments, the compound of formula XI is greater than 95% mol fraction of a sample or greater than 99% mol fraction of the sample.

D. Supramolecular Structures/Compositions

Figure 6:
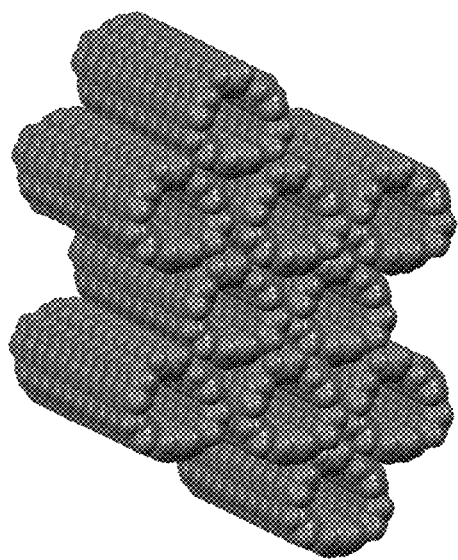
FIG. 6 is an illustration of a side view of a tubular structure formed from synthesized [6]CPP.
Figure 7:
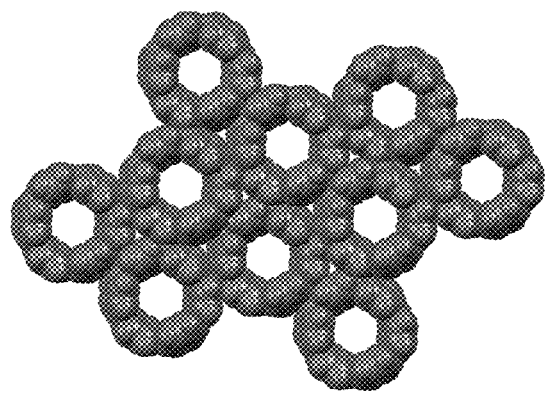
FIG. 7 is an illustration of a top-down view of a tubular structure formed from synthesized [6]CPP.

This invention also includes a composition comprising at least two molecules of 6-cycloparaphenylene interacting to form a structure. The structure formed is exemplified by FIGS. 6, and 7, which illustrates the crystal packing pattern of [6]CPP that form the composition. Illustrated are the side (FIG. 6) and top view (FIG. 7). Such compositions can be formed by recrystallizing [6]CPP dissolved in solvent or a mixture of solvents. A non-limiting example of a suitable solvent mixture is a dichloromethane/hexane solution.

As the illustration of the crystal structure shows, at least two molecules of [6]CPP can self-assemble in a linearly fashion to form a nanotube. The crystal structure further shows that the nanotubes can self-assemble to form a composition with multiple orderly arranged nanopores.

Carbon nanotubes are known to be electrically and/or thermally conductive. The nanotube/nanopore structures/compositions form as described herein can be electrically and/or thermally conductive. Consequently, in some embodiments, this invention pertains to these nanotube structures of [6]CPP. As the crystal structure shows, such nanotube structures can be uniform or substantially uniform in size. By 'substantially uniform in size' we mean that least 80% of the nanotubes of a representative sample are the same length. In some embodiments, at least 90% of the nanotubes of a representative sample are the same length. In some embodiments, at least 95% of the nanotubes of a representative sample are the same length.

As the crystal structure shows, the nanotube can be straight or substantially straight. By 'substantially straight' we mean that at least 80% of the nanotubes of a representative sample do not curve more than 5° from end to end. In some embodiments, at least 85% of the nanotubes of a representative sample do not curve more than 3° from end to end. In some embodiments, at least 90% of the nanotubes of a representative sample do not curve more than 1° from end to end.

As the crystal structure shows, the nanopores can be uniform in diameter or substantially uniform in diameter. By 'substantially uniform in diameter' we mean that the mean diameter of at least 80% of the nanopores of a representative sample do not deviate more than 10%. In some embodiments, the mean diameter of at least 90% of the nanopores of a representative sample do not deviate more than 9%. In some embodiments, the mean diameter of at least 95% of the nanopores of a representative sample do not deviate more than 2%.

Methods

In some embodiments, this invention also pertains to methods of making intermediates for the size selective preparation of CPPs (i.e. [n]CPPs) where [n] can be selected based on the input reagents.

A. Synthesis of Compound IV

Accordingly, in some embodiments, this invention pertains to a method for the production of a compound of general formula VI (shown below). Compounds of formula VI are useful intermediates to the formation of [n]macrocycles and [n]cycloparaphenylenes. Said method comprises: contacting a compound of formula II*:

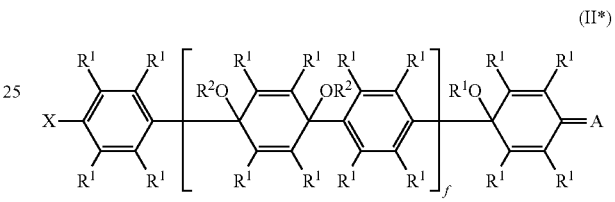

(II*)

with a base to generate the deprotonated ketone. The deprotonated ketone is then contacted with an organometallic compound of formula III:

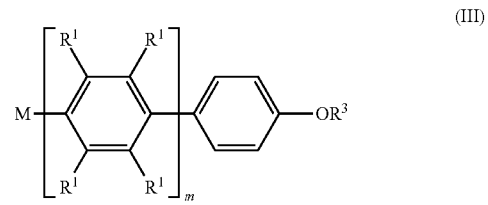

(III)

under conditions that produce a compound of formula IV:

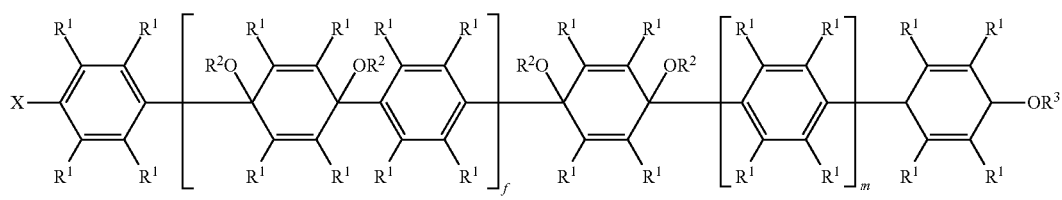

(IV)

An example of 'conditions that produce a compound of formula IV' can be found in Example 1. Typically, the method is performed under anhydrous conditions at reduced temperature (often −78° C.) in an organic solvent or mixture of organic solvents. The solvent will typically be ether-based solvent such as ether, tetrahydrofuran or dioxane which can optionally be mixed with other solvents such as an apolar solvent or solvents like pentane, hexane, hexanes or mineral oil(s). In some embodiments, compounds of formula III can be generated in-situ, as shown in Example 1. As shown in Example 1, alkylation with an alkylating reagent (e.g. methyl iodide or ethyl iodide) is also a component of the 'conditions that produce a compound of formula IV'.

In some embodiments of this method, f can be 0, 1, 2, 3, 4, 5, 6, 7, 8, 9 or 10 and m can be an integer from 0, 1, 2, 3, 4 or 5; A can be oxygen or sulfur; X can be F, Cl, Br or I; M can be lithium, zinc, or MgBr; each $R^1$ can be independently selected from the group consisting of hydrogen, lower alkyl, alkylene, cycloalkyl, heterocycloalkyl, aryl and heteroaryl or independently two $R^1$ groups on adjacent carbons combined with atoms to which each is attached to form a 4, 5 or 6 membered cycloalkyl, heterocycloalkyl, aryl or heteroaryl ring; each $R^2$ can be independently selected from the group consisting of lower alkyl, alkylene, cycloalkyl, heterocycloalkyl, aryl and heteroaryl; and $R^3$ can be a phenol or thiophenol protecting group.

In some embodiments of the method, subscript f can be from 1 to about 5. In some embodiments, subscript f can be from 1 to about 6 or from 1 to about 3. In some embodiments, subscript f can be 0, 1, 2 or 3. In some embodiments, m is 1. In some embodiments, m is 2. In some embodiments m is 3. In some embodiments, subscript m can be 0, 1, or 2.

In some embodiments of the method, protecting group —$OR^3$ is a silyl ether. In other embodiments, protecting group $R^3$ is trimethyl silyl (TMS) or tert-butyl dimethyl silyl (TBDMS) group.

In some embodiments of the method, X is bromine. In some embodiments, X is chlorine. In some embodiments, X is iodine. In some embodiments, X is fluorine.

In some embodiments of the method, A is oxygen (O). In some embodiments A is sulfur (S). In some embodiments, M is lithium.

In some embodiments of the method, each $R^2$ can independently be methyl or ethyl. In some embodiments, each $R^2$ can independently be lower alkyl or aryl. In some embodiments, each $R^2$ in formula IV can be lower alkyl. In some embodiments, each $R^2$ in formula IV can independently be lower alkyl or cycloalkyl. In some embodiments, each $R^2$ in formula IV can be alkylene. In some embodiments, each $R^2$ in formula II* can be cycloalkyl. In some embodiments, each $R^2$ in formula II* can be heterocycloalkyl. In some embodiments, each $R^2$ in formula II* can be heteroaryl.

In some embodiments of the method, each $R^1$ can be hydrogen, methyl or ethyl. In some embodiments, each $R^1$ can be hydrogen. In some embodiments, each $R^1$ can be methyl. In some embodiments, each $R^1$ can be ethyl. In some embodiments, each $R^1$ can be independently hydrogen, methyl or ethyl. In some embodiments, each $R^1$ can be independently hydrogen, methyl, ethyl, propyl, isopropyl, butyl, tert-butyl, sec-butyl or isobutyl. In some embodiments, each $R^1$ can be independently lower alkyl, cycloalkyl or aryl. In some embodiments, each $R^1$ can be independently lower alkyl or aryl. In some embodiments, each $R^1$ can be lower alkyl. In some embodiments, each $R^1$ can independently be lower alkyl or cycloalkyl. In some embodiments, each $R^1$ can be alkylene. In some embodiments, each $R^1$ can be cycloalkyl. In some embodiments, each $R^1$ can be heterocycloalkyl. In some embodiments, each $R^1$ can be heteroaryl.

In some embodiments of the method, two $R^1$ groups on adjacent carbons that combine with atoms to which each is attached form a 5 or 6 membered cycloalkyl ring, wherein said 5 or 6 membered ring is has the formula XXI:

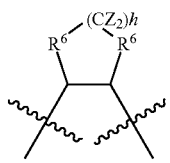

wherein, each $R^6$ is $CZ_2$; each Z is independently hydrogen, F, Cl, Br or I; and each h is independently 1 or 2.

As previously noted the 'conditions that produce a compound of formula IV' involve an alkylation reaction. As shown in Example 1, the alkylation is performed in-situ without isolation of what would otherwise be a diol intermediate. It is to be understood that generally (but not necessarily), the alkylation will be carried out in-situ when performing the methods disclosed herein as this tends to be more efficient. However, it is also to be understood that in some embodiments, the conditions that produce a compound of formula IV will involve isolation of the diol intermediate followed by alkylation of the hydroxyl groups of the diol to form the compound of formula IV. Exemplary methods and reagents for performing such alkylation reactions are known in the art (and substantially similar to methods disclosed herein) and discussed in Michael B. Smith and Jerry March, *March's Advanced Organic Chemistry* (6th ed. 2007) at pages 587-656, 912-913 and 980-984 (and references discussed/referred to therein).

Generally speaking, the hydroxyl groups of the diol are deprotonated under conditions of strong base under anhydrous conditions in an organic solvent at reduced temperature and then an alkylating reagent (e.g. methyl iodide or ethyl iodide) is added to effect alkylation of said hydroxyl groups. The reaction is quenched with the addition of water and the product is isolated and purified as necessary.

B. Cyclic Utility of Compounds of Formula IV—Building Larger Structures

The method disclosed above provides a way to produce compounds of formula IV from starting compounds of formula II*, wherein the ring length (i.e. the number of linearly connected 6-membered rings from end to end) of the product compound of formula IV is the sum of the ring lengths of the compound of formula II* and the compound of formula III. Consequently, the product compounds of formula IV, when produced from the compounds of formula II* and III, as described above, is itself longer in ring length than the starting compound of formula II* (See FIG. 4).

Figure 4:
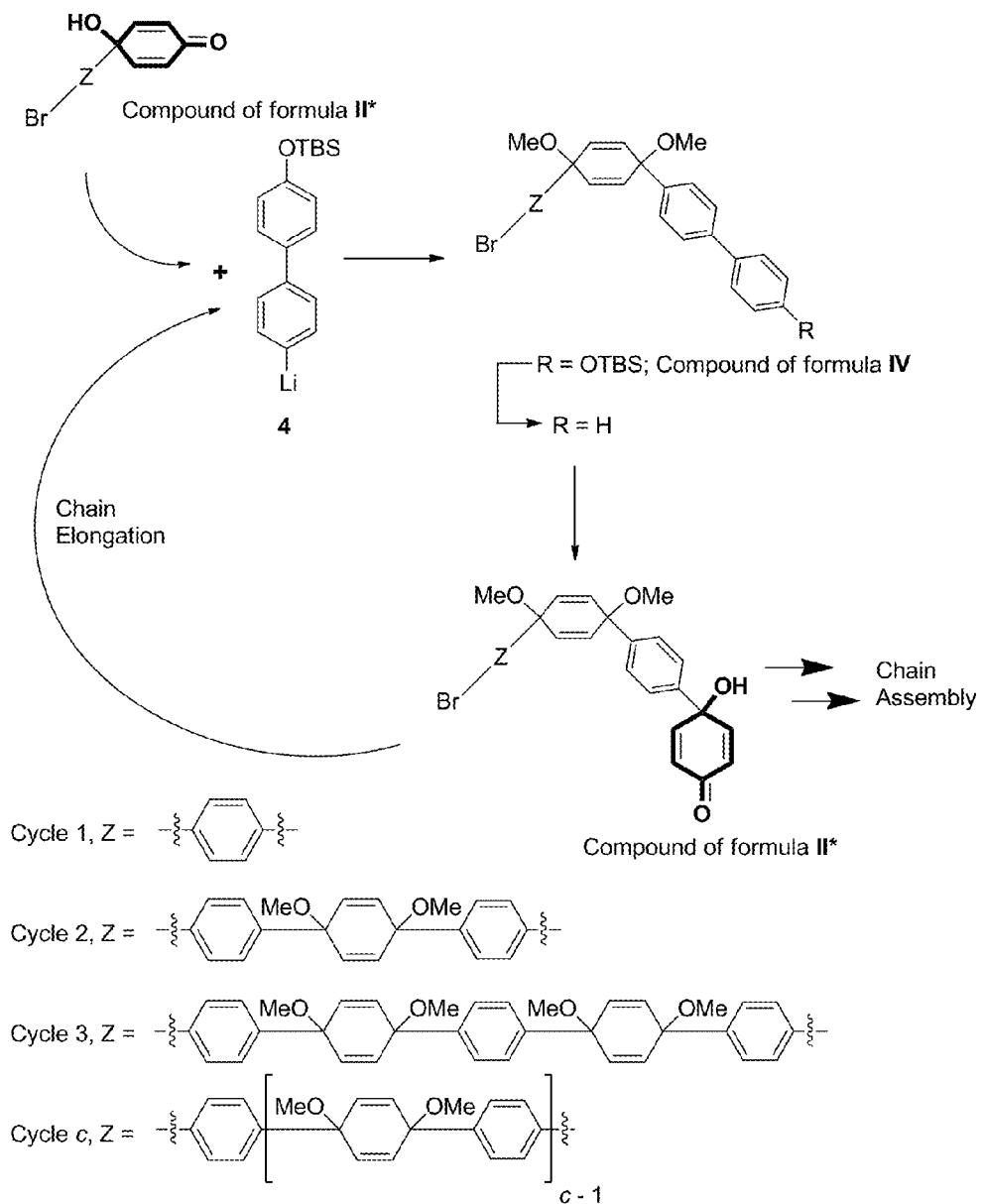
FIG. 4 is a synthetic scheme for producing various sized intermediates useful for the preparation of longer intermediates through chain elongation. Said intermediates can be used as inputs to produce intermediates (i.e. precursors) that can themselves be used in the preparation of [n]macrocycle and [n]CPP compounds.

It is also to be understood that compounds of formula IV can be converted into compounds of formula II* using methods described herein such that these newly formed compounds of formula II* have the same ring length as the compound of formula IV from which they are prepared. Since the compounds of formula IV are intermediates to [n]macrocycle and [n]cycloparaphenylene production (as described, for example, in Examples 4-6 below and illustrated with respect to 2-piece assembly in FIG. 5), it is possible to build larger and larger [n]macrocycle and the corresponding [n]cycloparaphenylene structures by judicious selection of reagents and repeated cycling of: 1) converting the synthesized compound of formula IV to a compounds of formula II*; 2) producing compounds of formula IV from said converted compound II*; and repeating steps 1 and 2 any number of times (e.g. from 1 to about 10 times) until the desired ring length for a compound of formula IV is achieved. An example of this repeatable cycle in which a compound of formula III consists of two rings is shown in FIG. 4. The scheme for 2-piece assembly of the resulting compounds can be found in FIG. 5). However, it is also to be understood that at each cycle, the increase in ring length from the starting compound II* to the product compound IV will be determined by the number of rings in the compound of formula III. It is to be understood that compounds of formula III can comprise from 1-6 six membered rings wherein said rings can be aromatic or cyclohexadiene.

An example of the conversion of a compound of formula IV to a compound of formula II* is illustrated in the conversion of compound 5 to compound 7 as described in Examples 2 and 3 (Also see FIG. 4). Generally, to covert a product compound of formula IV into a new reactant compound of formula II*, the first step is to remove the terminal phenol or thiophenol protecting group ($R^3$ as used with reference to compounds of formula III (or just R in FIG. 4)). The conditions for removal of this protecting group will depend on its nature. For example, if the protecting group is acid-labile it will be removed by subjecting the compound of formula IV to acid. Similarly, if the protecting group is base-labile it will be removed by subjecting the compound of formula IV to base. As shown in the conversion of compound 5 to compound 7, the protecting group is a silyl ether that can be removed with fluoride. Consequently, for that step, the $R^3$ (as used with reference to compounds of formula III) protecting group was removed by treatment with tetra-n-butylammonium fluoride under anhydrous conditions and the product phenol (compound 6) was isolated. Many exemplary methods for removing acid-labile, base-labile and fluoride-labile protecting groups are known in the art and can be found in Theodora W. Green & Peter G. M. Wuts, *Greene's Protective Groups in Organic Synthesis* (4th ed. 2007), pages 370-419, and references discussed/referred to therein.

The phenol or thiophenol compound that results from this deprotection reaction of the $R^3$ (as used with reference to compounds of formula III) protecting group can then be converted to the ketone compound of formula II* by oxidation. For purposes of illustration, in Example 3, the phenol compound 6 is converted to the ketone compound 7 by treatment with (diacetoxyiodo)benzene in organic solvent at ambient temperature. Such a methodology will generally be successful for the conversion of the phenol or thiophenol compounds derived from the compounds of formula IV (contemplated to be prepared by the method disclosed in Section A above) into the compounds of formula II* that can be used in the cyclic generation of larger compounds of formula IV as contemplated by this Section B.

It is further to be understood that when the ketone compounds of formula II* is sufficiently long enough, it can be "capped" by, for example, converting it to a di-halo compound as shown in Example 4 (i.e. a "capping step"). Di-halo compounds can be converted to di-boronates as described in Section E. below. Said di-halo compounds and di-boronates can be used in the 2-piece assembly methods illustrated in FIG. 5 and described in more detail in Section E, below.

C. Synthesis of Compound VI

The present invention is further directed to methods that can be used to produce compounds of formula VI. Like compounds of formula IV, compounds of formula VI can be used as intermediates in the production of [n]macrocycles and [n]cycloparaphenylenes.

Consequently, in some embodiments, this invention pertains to a method comprising: contacting a compound of formula II:

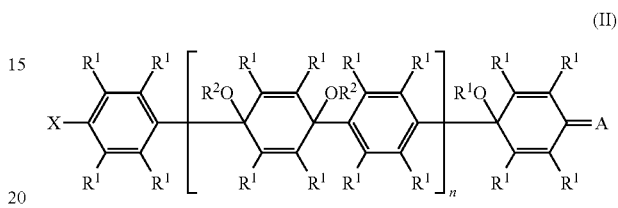

with compound of formula V:

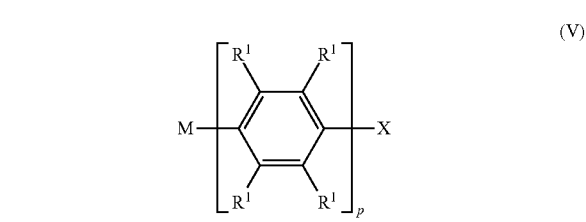

under conditions that produce a compound of formula VI:

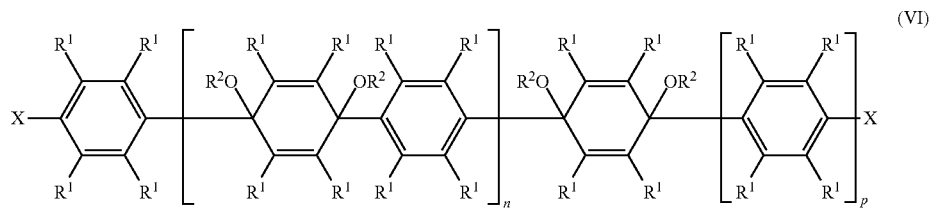

An example of 'conditions that produce a compound of formula VI' can be found in Example 4. Typically, the method is performed under anhydrous conditions at reduced temperature (often −78° C.) in an organic solvent or mixture of organic solvents. The solvent will typically be an ether-based solvent such as ether, tetrahydrofuran or dioxane which can optionally be mixed with other solvents such as an apolar solvent or solvents like pentane, hexane, hexanes or mineral oil(s).

In some embodiments, compounds of formula V can be generated in-situ from readily available di-halo starting materials, as shown in Example 4. For example, diiodobenzene, dibromobenzene, 1-iodo-4-bromobenzene, 1-chloro-4-bromobenzene are some non-limiting examples of di-halo starting materials.

Generally speaking, the 'conditions that produce a compound of formula VI' require that the compound of formula II is deprotonated before being reacted with compound the compound of formula V. This can be accomplished by treating the compound of formula II with a strong base (e.g.

sodium hydride, potassium hydride or sodium metal or amine bases) under anhydrous conditions as illustrated in Example 4. As shown in Example 4, alkylation with an alkylating reagent (e.g. methyl iodide or ethyl iodide) is also a component of the 'conditions that produce a compound of formula VI'. When the reaction completed, it is generally quenched by the introduction of water, followed by product isolation and optional purification.

In some embodiments of this method, n can be 1, 2, 3, 4, 5, 6, 7, 8, 9 or 10 and p can be an integer from 1, 2 or 3; A can be oxygen or sulfur; M can be lithium, zinc, or MgBr; each $R^1$ can be independently selected from the group consisting of hydrogen, lower alkyl, alkylene, cycloalkyl, heterocycloalkyl, aryl and heteroaryl or independently two $R^1$ groups on adjacent carbons combined with atoms to which each is attached to form a 4, 5 or 6 membered cycloalkyl, heterocycloalkyl, aryl or heteroaryl ring; each $R^2$ can be independently selected from the group consisting of lower alkyl, alkylene, cycloalkyl, heterocycloalkyl, aryl and heteroaryl; and $R^3$ can be a phenol or thiophenol protecting group; and each X is independently F, Cl, Br or I.

In some embodiments of the method, subscript n can be from 1 to about 5. In some embodiments, subscript n can be from 1 to about 6 or from 1 to about 3. In some embodiments, subscript n can be 1, 2 or 3. In some embodiments, p is 1. In some embodiments, p is 2. In some embodiments p is 3. In some embodiments, subscript p can be 1 or 2.

In some embodiments of the method, X is bromine. In some embodiments, X is chlorine. In some embodiments, X is iodine. In some embodiments, X is fluorine.

In some embodiments of the method, A is oxygen (O). In some embodiments A is sulfur (S). In some embodiments, M is lithium.

In some embodiments of the method, each $R^2$ can independently be methyl or ethyl. In some embodiments, each $R^2$ can independently be lower alkyl or aryl. In some embodiments, each $R^2$ in formula IV can be lower alkyl. In some embodiments, each $R^2$ in formula IV can independently be lower alkyl or cycloalkyl. In some embodiments, each $R^2$ in formula IV can be alkylene. In some embodiments, each $R^2$ in formula II can be cycloalkyl. In some embodiments, each $R^2$ in formula II can be heterocycloalkyl. In some embodiments, each $R^2$ in formula II can be heteroaryl.

In some embodiments of the method, each $R^1$ can be hydrogen, methyl or ethyl. In some embodiments, each $R^1$ can be hydrogen. In some embodiments, each $R^1$ can be methyl. In some embodiments, each $R^1$ can be ethyl. In some embodiments, each $R^1$ can be independently hydrogen, methyl or ethyl. In some embodiments, each $R^1$ can be independently hydrogen, methyl, ethyl, propyl, isopropyl, butyl, tert-butyl, sec-butyl or isobutyl. In some embodiments, each $R^1$ can be independently lower alkyl, cycloalkyl or aryl. In some embodiments, each $R^1$ can be independently lower alkyl or aryl. In some embodiments, each $R^1$ can be lower alkyl. In some embodiments, each $R^1$ can independently be lower alkyl or cycloalkyl. In some embodiments, each $R^1$ can be alkylene. In some embodiments, each $R^1$ can be cycloalkyl. In some embodiments, each $R^1$ can be heterocycloalkyl. In some embodiments, each $R^1$ can be heteroaryl.

In some embodiments of the method, two $R^1$ groups on adjacent carbons that combine with atoms to which each is attached form a 5 or 6 membered cycloalkyl ring, wherein said 5 or 6 membered ring is has the formula XXI:

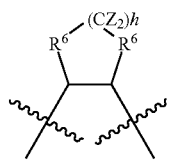

(XXI)

wherein, each $R^6$ is $CZ_2$; each Z is independently hydrogen, F, Cl, Br or I; and each h is independently 1 or 2.

D. Synthesis of Boronates

Dihalo compounds of formula VI or formula VII can be converted to diboronates. These diboronates can be generated in-situ (e.g. Example 5) or prepared for isolation (e.g. Example 7). The diboronates themselves can be used as intermediates in the synthesis of [n]macrocycles and their related [n]cycloparaphenylenes as discussed in more detail in Section E, below.

Thus, in some embodiments, the method further comprises contacting a compound of formula VI with a borate (e.g. pinacol borate) under conditions that produce a compound of formula VI*:

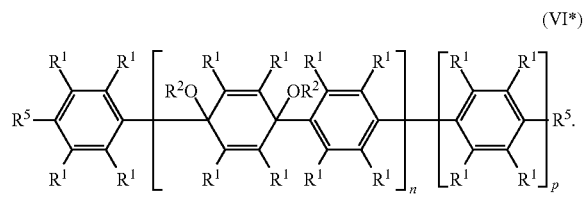

(VI*)

In this method, $R^1$, $R^2$, n and p can be as described above in Section C with respect to compound of formula VI. In this method, $R^5$ is a boronate. In some embodiments, this boronate is pinacol boronate:

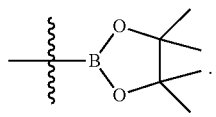 [SMILES: *B1OC(C)(C)C(C)(C)O1]

As noted, examples of 'conditions that produce a compound of formula VI*' can be found in Examples 5 and 7. Typically, the method is performed under anhydrous conditions at reduced temperature (often −78° C.) in an organic solvent or mixture of organic solvents. The solvent will typically be ether-based solvent such as ether, tetrahydrofuran or dioxane which can optionally be mixed with other solvents such as an apolar solvent or solvents like pentane, hexane, hexanes or mineral oil(s). When the reaction completed, it is generally quenched by the introduction of water, followed by product isolation and optional purification.

Figure 5:
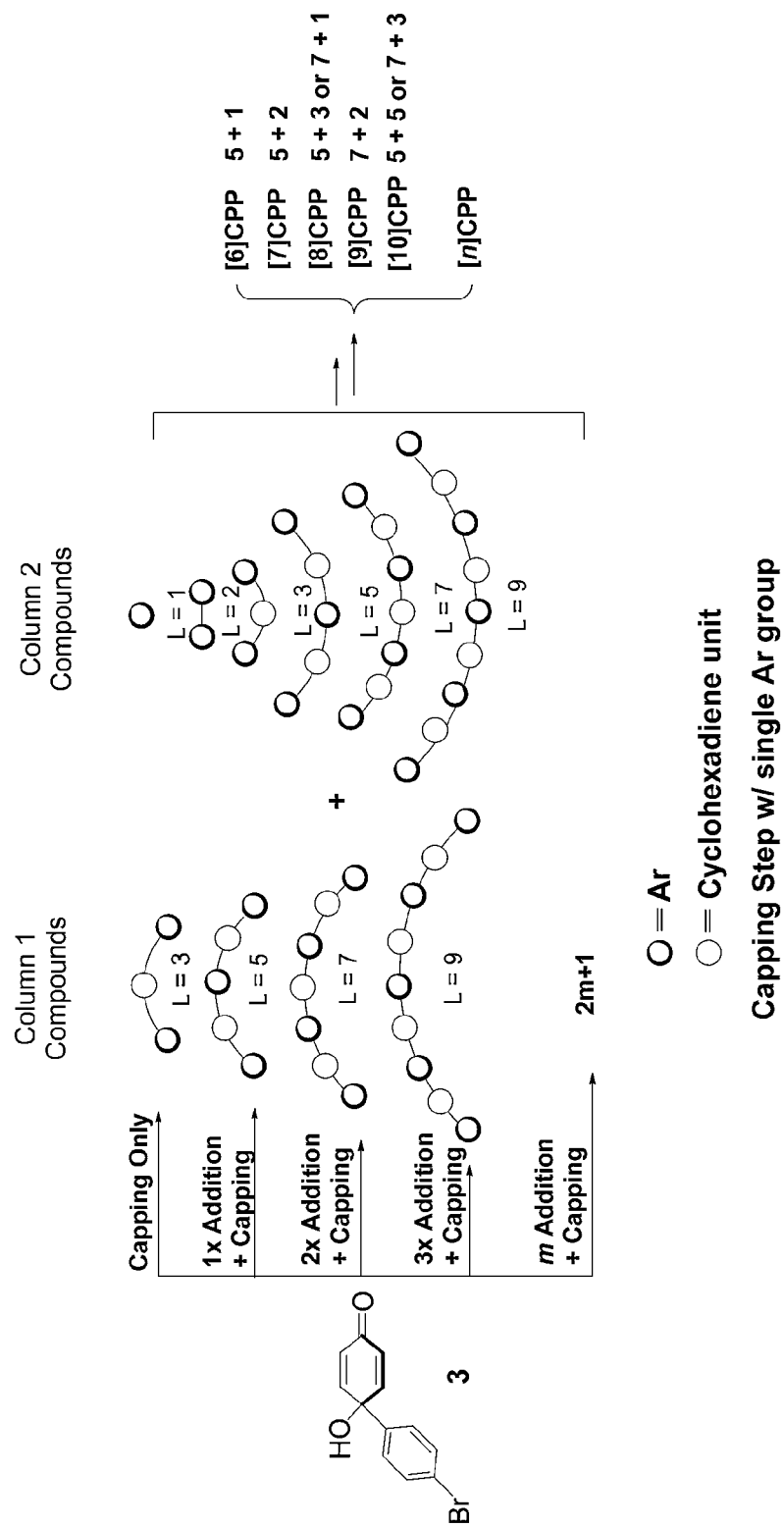
FIG. 5 is an illustration of a synthetic scheme for the 2-piece assembly of various sized intermediates useful for producing [n]macrocycles and [n]CPPs.

It is also to be understood that the synthesis of boronates can be accomplished with compounds that are shorter in chain length than are the compounds of formula IV. For example, diiodobenzene, dibromobenzene, 1-iodo-4-bromobenzene, 1-chloro-4-bromobenzene are some non-limiting examples of di-halo starting materials that can be used to create a di-boronate with a single aromatic ring that can be used in the preparation of precursors to the 2-piece assembly of [n]macrocycle precursors as illustrated in FIG. 5. Said diiodobenzene, dibromobenzene, 1-iodo-4-bromobenzene, 1-chloro-4-bromobenzene can also be used directly in the preparation of precursors to the 2-piece assembly of [n]macrocycle precursors as illustrated in FIG. 5. 4,4'-Dibromobiphenyl, itself, or if converted to its corresponding di-boronate, is an example of a compound that can be used to add two aromatic rings to prepare a [n]macrocycle precursor as part of the 2-piece assembly of [n]macrocycle precursors as illustrated in FIG. 5.

E. Synthesis of [n]macrocycles

In some embodiments, this invention pertains to methods for the synthesis of [n]macrocycles that themselves can be converted to [n]cycloparaphenylenes (as shown in Examples 10 and 11). Thus, in some embodiments, this invention pertains to a method comprising; contacting a compound of formula VII:

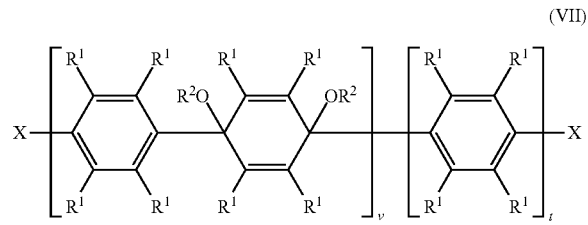
(VII)

with a compound of formula VIII:

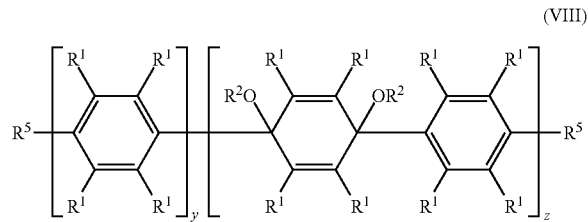
(VIII)

and a palladium catalyst under conditions that produce a compound of formula XI:

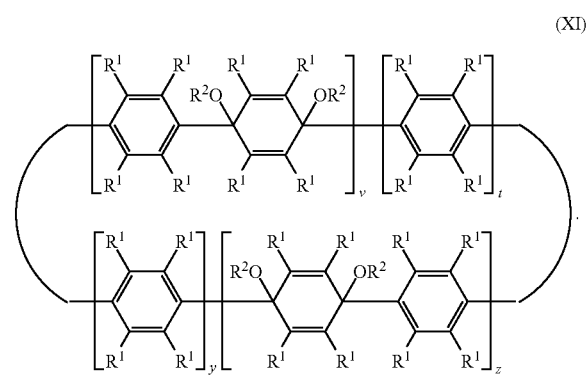
(XI)

An example of 'conditions that produce a compound of formula XI' can be found in Examples 8 and 9. Typically, the method is performed at elevated temperature in an organic solvent or mixture of organic solvents. The solvent (or mixture of solvents will typically be, or comprise, a polar solvent. Solvents such as alcohols (isopropanol), N,N-dimethylformamide (DMF), water, or mixtures thereof can be used.

In this method, each $R^5$ is a boronate. In some embodiments, the group, $R^5$, is isopropyl pinacol boronate.

In some embodiments, X can be F, Cl, Br or I. In some embodiments of the method, X is bromine. In some embodiments, X is chlorine. In some embodiments, X is iodine. In some embodiments, X is fluorine.

In this method, subscript t can be an integer from 1-3; subscript v can be an integer from 0-12; subscript y can be an integer from 1-3; and subscript z can be an integer from 0-12; provided that; (i) v and z cannot both be zero; (ii) if v=0, then y+2z is greater than or equal to 5; and (iii) if z=0, then t+2v is greater than or equal to 5. In some embodiments, t is 1; v is 2; y is 1; and z is 0. In some embodiments, t is 1; v is 2; y is 1; and z is 1. In some embodiments, t is 1; v is 2; y is 1; and z is 2.

In some embodiments of the method, each $R^2$ can independently be methyl or ethyl. In some embodiments, each $R^2$ can independently be lower alkyl or aryl. In some embodiments, each $R^2$ can be lower alkyl. In some embodiments, each $R^2$ can independently be lower alkyl or cycloalkyl. In some embodiments, each $R^2$ can be alkylene. In some embodiments, each $R^2$ can be cycloalkyl. In some embodiments, each $R^2$ can be heterocycloalkyl. In some embodiments, each $R^2$ can be heteroaryl.

In some embodiments of the method, each $R^1$ can be hydrogen, methyl or ethyl. In some embodiments, each $R^1$ can be hydrogen. In some embodiments, each $R^1$ can be methyl. In some embodiments, each $R^1$ can be ethyl. In some embodiments, each $R^1$ can be independently hydrogen, methyl or ethyl. In some embodiments, each $R^1$ can be independently hydrogen, methyl, ethyl, propyl, isopropyl, butyl, tert-butyl, sec-butyl or isobutyl. In some embodiments, each $R^1$ can be independently lower alkyl, cycloalkyl or aryl. In some embodiments, each $R^1$ can be independently lower alkyl or aryl. In some embodiments, each $R^1$ can be lower alkyl. In some embodiments, each $R^1$ can independently be lower alkyl or cycloalkyl. In some embodiments, each $R^1$ can be alkylene. In some embodiments, each $R^1$ can be cycloalkyl. In some embodiments, each $R^1$ can be heterocycloalkyl. In some embodiments, each $R^1$ can be heteroaryl.

In some embodiments of the method, two $R^1$ groups on adjacent carbons that combine with atoms to which each is attached form a 5 or 6 membered cycloalkyl ring, wherein said 5 or 6 membered ring is has the formula XXI:

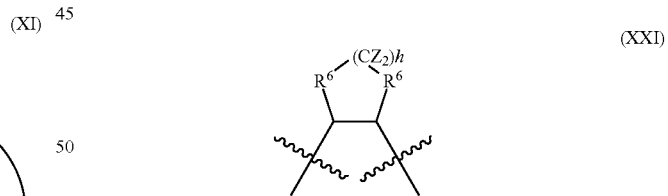
(XXI)

wherein, each $R^6$ is $CZ_2$; each Z is independently hydrogen, F, Cl, Br or I; and each h is independently 1 or 2.

As previously noted, the [n]macrocycles of formula XI can be used to produce [n]cycloparaphenylenes. However, since the size on the input compounds of formula VII and VIII can be custom-selected, it is possible to prepare custom [n]macrocycles and [n]cycloparaphenylenes of selected [n] ring size.

An illustration of a scheme for the 2-piece assembly of [n]macrocycle precursors that can be used for preparing select custom [n]macrocycles and [n]cycloparaphenylenes can be found in FIG. 5. In principle, the linked dots in each Column in FIG. 5 represent compounds of formula VII and VIII, wherein each dot represents a 6 membered ring. Therefore, the linked dots in Column 1 represent a compound from 3 (L=3) to 9 (L=9) six membered rings in length. Similarly, the linked dots in Column 2 represent a compound from 1 (L=1) to 9 (L=(9) six membered rings in length. Compound length can be controlled by judicious application of the methods described in sections A, C, and D above and the Examples described below.

For example, compounds of length 1 and 2 in Column 2 can be made by methods described in section D from readily available starting materials (1,4-dibromobenzene and 4,4'-Dibromobiphenyl). Compounds of length 3 and greater can be created by applying the method in section B (the "capping step") or the method described in Section C to create the dibromo form, and optionally using the methods described in section D to convert the dibromo to the diboronate form. The dibromo and diboronate compounds are themselves [n]macrocycles precursors used as described above to produce [n]macrocycles.

With a variety of [n]-length components at hand, a [n]macrocycle can be synthesized by judicious selection of any two [n]macrocycle intermediates such that the sum of their lengths is the desired size of the [n]macrocycle. For example, an [8]macrocycle can be made by both the reaction of components of length 5 and 3, and the reaction of components of length 7 and 1. As illustrated in FIG. 5, using the methods disclosed above, select [n]macrocycles of just about any size comprising [n]=6 or more can be assembled using this method. Because the [n]macrocycles can be directly converted to their corresponding [n]cycloparaphenylenes, select [n]cycloparaphenylenes of any size can likewise be produced.

Advantages

The novel methods and compositions disclosed herein permit the preparation of [n]macrocycles and [n]cycloparaphenylenes of select and defined ring size and in amounts not previously possible.

EXAMPLES

Aspects of the present teachings can be further understood in light of the following examples, which should not be construed as limiting the scope of the present teachings in any way.

General Experimental Details

Moisture sensitive reactions were carried out under an inert atmosphere of nitrogen using standard Schlenk technique. The starting materials 3 (Sisto, T. J.; Golder, M. R.; Hirst, E. S.; Jasti, R. *J. Am. Chem. Soc.* 2011, 133, 15800-15802) and 4-Bromo-4'[(tert-butyldimethylsilyl)oxy]biphenyl (Ikuma, N.; Tsue, H.; Tsue, N.; Shimono, S.; Uchida, Y.; Masaki, K.; Matsuoka, N.; Tamura, R. *Org. Lett.* 2005, 7, 1797-1800) were prepared according to literature procedures. All other starting materials and chemicals were commercially available.

$^1$H NMR spectra were recorded at 500 MHz or 400 MHz on a Varian VNMRS. $^{13}$C NMR spectra were recorded at 125 MHz or 100 MHz on a Varian VNMRS. All nuclear magnetic resonance (NMR) spectra were referenced to tetramethyl silane (TMS). The matrix used for matrix assisted laser desorption ionization (MALDI) mass spectrometry (MS) was a solution of 10 mg/ml of 7,7,8,8-tetracyanquinodimethane in tetrahydrofuran (THF) with 1% silver trifluoroacetate as a promoter. Absorbance spectra were obtained in dichloromethane using a Varian Cary 100 Bio UV-Vis spectrometer. All reagents were obtained commercially. Tetrahydrofuran, dichloromethane (DCM), and dimethylformamide (DMF) were dried by filtration through alumina according to the methods described by Grubbs (Pangborn, A. B.; Giardello, M. A; Grubbs, R. H.; Rosen, R. K.; Timmers, F. J. *Organometallics* 1996, 15, 1518-1520). Silica column chromatography was conducted with Zeochem Zeoprep 60 Eco 40-63 µm silica gel. Thin Layer Chromatography (TLC) was performed using Sorbent Technologies Silica Gel XHT TLC plates. Developed plates were visualized using UV light at wavelengths of 254 and 365 nm. All glassware was oven or flame dried and cooled under an inert atmosphere of nitrogen unless otherwise noted.

Electrochemical measurement was performed on a Princeton Applied Research Potentiostat/Galvanastat Model 273 and the software used was the M270/250 Electrochemical Software, also from Princeton Applied Research. The electrolyte (n-Bu$_4$NPF$_6$) was received from Sigma-Aldrich and recrystallized from methylene chloride three times. Dichloromethane for the electrochemical analysis was obtained from Fisher and was distilled over calcium hydride (CaH$_2$) before use. The dichloromethane was thoroughly degassed by subjecting it to at least six successive freeze-pump-thaw cycles, after which they were transferred to an inert atmosphere glove box. The glove box is also an N$_2$ atmosphere.

General details for the X-ray diffraction analysis: Data collection: APEX2 (Bruker, 2006); cell refinement: SAINT (Bruker, 2006); data reduction: SAINT (Bruker, 2006); program(s) used to solve structure: SHELXS97 (Sheldrick, 1990); program(s) used to refine structure: SHELXL97 (Sheldrick, 1997); molecular graphics: OLEX2 (Dolmanov, et al. 2009); software used to prepare material for publication: PubICIF v.1.9.5_c (IUCr).

Example 1

Preparation of Compound 5

Figure 2:
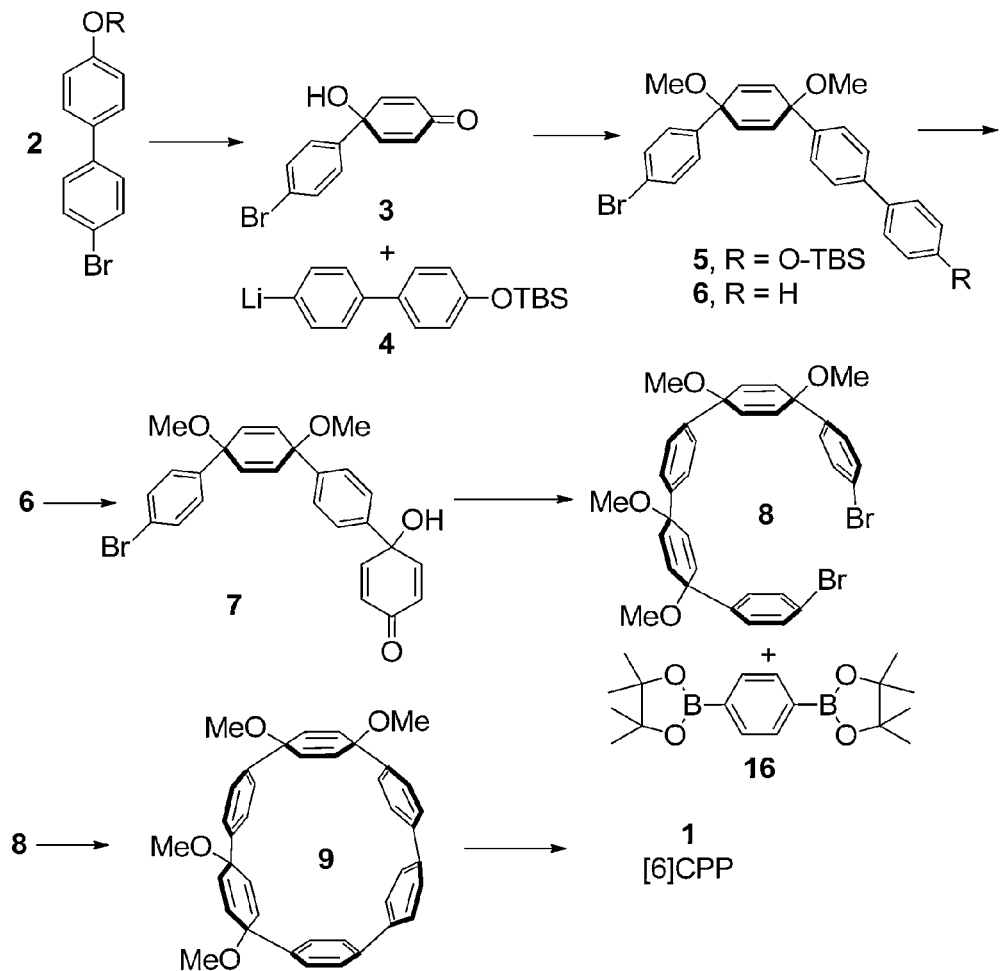
FIG. 2 is a synthetic scheme for the synthesis of [6]CPP and possible larger [n]CPPs.

See FIG. 2 for Synthetic Scheme

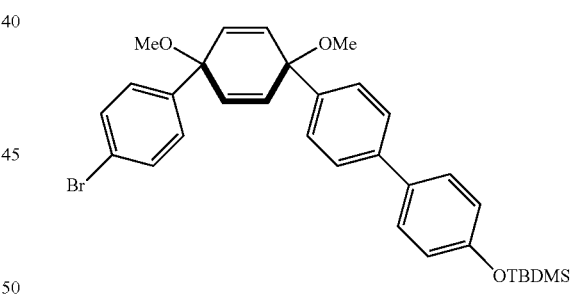

To a slurry of sodium hydride (5.88 g, 147 mmol, 60% in mineral oil) in 300 mL of tetrahydrofuran (THF) was added slowly a solution of the ketone 3 (30 g, 113 mmol) in 500 mL of THF at −78° C., the reaction mixture was stirred for another 2 h at −78° C. to generate the deprotonated ketone.

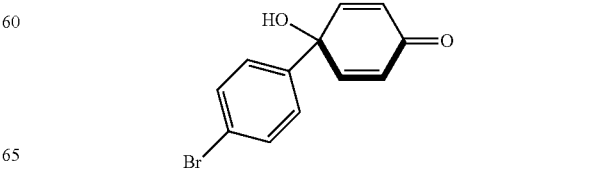

In a separate 1000 mL flask, 4-Bromo-4'[(tert-butyldimethylsilyl)oxy]biphenyl[1] (86 g, 237 mmol) was dissolved in 500 mL dry THF. This solution was cooled down to −78° C. n-butyl lithium (n-BuLi, 100 mL, 249 mmol, 2.5 M in hexane) was added slowly to this solution, then the reaction mixture was allowed to stir for 30 min at −78° C. to give lithium reagent 4.

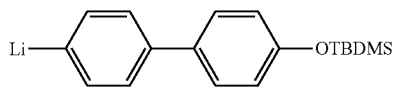

4

This lithium reagent 4 was transferred to the slurry containing deprotonated ketone 3 (prepared as described above) via cannula, and the resulting mixture was allowed to stir for another 2 h at −78° C. $CH_3I$ (28.2 mL, 452 mmol) and dry DMF (200 mL) were then added to quench the addition reaction, the reaction mixture was allowed to warm up to room temperature and stir for overnight. Water (400 mL) was added carefully to quench the methylation reaction, and the resulting mixture was extracted with diethyl ether (3×250 mL). The combined organic layer was washed with water (3×150 mL) and brine (200 mL) and dried over sodium sulfate ($Na_2SO_4$). After concentrating under reduced pressure, the crude product was purified by column on silica gel (Ethyl Acetate/hexane=1:4) to give compound 5 as a white solid (49.7 g, 76%, m.p. 125-127° C.). $^1H$ NMR (400 MHz, $CDCl_3$): δ (ppm) 0.22 (s, 6H, Si—$CH_3$), 1.00 (s, 9H, C($CH_3$)), 3.42 (s, 3H, $OCH_3$), 3.43 (s, 3H, $OCH_3$), 6.05 (d, J=10 Hz, 2H, CH=CH), 6.16 (d, J=10 Hz, 2H, CH=CH), 6.89 (d, J=8.4 Hz, 2H, Ar—H), 7.27 (d, J=8.4 Hz, 2H, Ar—H), 7.39-7.48 (m, 6H, Ar—H), 7.50 (d, J=8.4 Hz, 2H, Ar—H). $^{13}C$ NMR (100 MHz, $CDCl_3$): δ (ppm) −4.39, 18.22, 25.68 (TBDMS), 51.97, 52.01 ($OCH_3$), 74.56, 74.59 (C-OMe), 120.31, 121.55, 126.28, 126.72, 127.83, 128.03, 131.39, 132.89, 133.69, 133.77, 140.26, 141.49, 142.56, 155.36 (Ar). High resolution mass spectrometry (HRMS) via quantitative time of flight (Q-TOF ES+) m/z calcd for $C_{32}H_{37}BrO_3Si$ (M-$OCH_3$)$^+$: 544.1433, Found: 544.1426. IR (neat): 2930, 2857, 1607, 1493, 1254, 1080, 822 $cm^{-1}$.

Example 2

Preparation of 6

See FIG. 2 for Synthetic Scheme

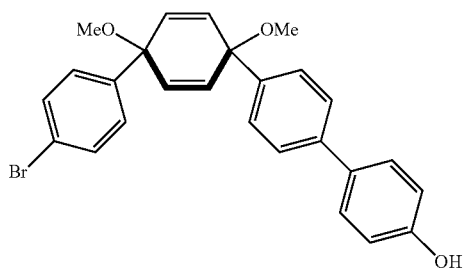

6

To a stirred solution of 5 (5.33 g, 9.2 mmol) in 120 mL THF was added 11 mL tetra-n-butylammonium fluoride TBAF (11 mmol, 1 M in THF). The reaction mixture was allowed to stir for 2 h at room temperature. Water (100 mL) was then added and the reaction mixture was extracted with diethyl ether (3×100 mL), the combined organic phase was washed with water (3×60 mL) and dried over sodium sulfate. After concentrating under reduced pressure, the crude yellow solid was purified by column on silica gel (Ethyl Acetate/hexane=1:2) to afford 6 as a white solid (4.05 g, 95%, m.p. 197° C.). $^1H$ NMR (400 MHz, $CDCl_3$): δ (ppm) 3.43 (s, 3H, $OCH_3$), 3.44 (s, 3H, $OCH_3$), 5.35 (s, 1H, OH), 6.07 (d, J=10.4, 2H, CH=CH), 6.17 (d, J=10.4, 2H, CH=CH), 6.83 (d, J=8.8, 2H, Ar—H), 7.27 (d, J=8.8, 2H, Ar—H), 7.39-7.49 (m, 8H, Ar—H). $^{13}C$ NMR (100 MHz, $CDCl_3$): δ (ppm) 51.97, 52.01 ($OCH_3$), 74.61, 74.68 (C-OMe), 115.64, 121.60, 126.32, 126.69, 127.82, 128.24, 131.42, 132.91, 133.19, 133.64, 140.18, 141.36, 142.40, 155.26 (Ar). HRMS (Q-TOF ES+) m/z calcd for $C_{26}H_{23}BrO_4$ (M-$OCH_3$)$^+$: 436.0602, Found: 436.0620. IR (neat): 3361, 1608, 1481, 1259, 1176, 822, 808 $cm^{-1}$.

Example 3

Preparation of 7

An Example of a Compound of Formula II and II*:
See FIG. 2 for Synthetic Scheme

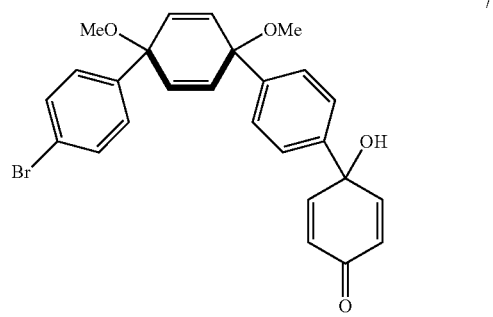

7

To a stirred solution of 6 (18 g, 38.84 mmol) in a mixture of THF (500 mL), acetonitrile ($CH_3CN$, 150 mL) and water ($H_2O$, 200 mL) was added (diacetoxyiodo)benzene (18.76 g, 58.26 mmol) slowly as a solid over the course of 1 h. The resulting mixture was stirred for 2 h at room temperature before quenching with saturated sodium bicarbonate ($NaHCO_3$) solution. The reaction mixture was extracted with dichloromethane (3×150 mL), and the combined organic phase was washed with water (3×100 mL) and dried over sodium sulfate. After removing solvent under reduced pressure, the crude yellow solid was purified by column on silica gel using ethyl acetate/hexane=1:1 as eluent to give compound 12 as a white solid (13.25 g, 71%, m.p. 190-191° C.). $^1H$ NMR (400 MHz, $CDCl_3$): δ (ppm) 2.99 (s, 1H, OH), 3.41 (s, 6H, $OCH_3$), 6.07 (dd, J=10 Hz, 4H, CH=CH), 6.19 (d, J=10 Hz, 2H, CH=CH), 6.85 (d, J=10 Hz, 2H, CH=CH), 7.25 (d, J=8.4 Hz, 2H, Ar—H), 7.36-7.44 (m, 6H, Ar—H). $^{13}C$ NMR (100 MHz, $CDCl_3$): δ (ppm) 51.99, 52.01 ($OCH_3$), 70.77 (C—OH), 74.39, 74.47 (C-OMe), 121.64, 125.42, 126.48, 126.76, 126.84, 127.72, 131.45, 133.18, 133.43, 138.12, 142.34, 143.49, 150.76 (Ar), 185.75 (C=O). HRMS (Q-TOF ES+) m/z calcd for $C_{26}H_{23}BrO_4$ (M)$^{30}$: 479.0858, Found: 479.0859. IR (neat): 3418, 2934, 1662, 1622, 1398, 1265, 1082, 1033, 947, 857, 737 cm$^{-1}$.

Example 4

Preparation of 8

An Example of a Compound of Formula VI or VII: See FIG. 2 for Synthetic Scheme

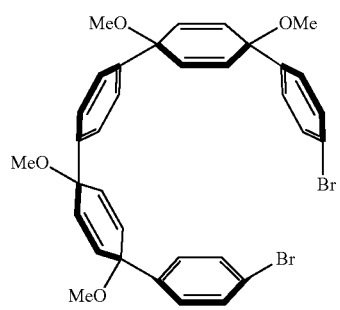

To a slurry of sodium hydride (2.17 g, 54.24 mmol, 60% in mineral oil) in 200 mL of THF was added a solution of ketone 7 (20 g, 41.72 mmol) in 300 mL dry THF at −78° C. The reaction mixture was stirred for another 2 h at −78° C. to generate the deprotonated ketone.

In a separate 500 mL round flask, 1,4-dibromobenzene (23.6 g, 100 mmol) was dissolved in 300 mL of THF, this solution was cooled down to −78° C., and then n-BuLi (42 mL, 105 mmol, 2.5 M in hexane) was added slowly to this solution. After the addition, the reaction mixture was stirred for 30 min to form the lithium reagent. This mixture was then transferred to the slurry containing the deprotonated ketone via cannula, and the resulting mixture was allowed to stir for another 2 h at −78° C. CH$_3$I (10.42 mL, 167 mmol) and dry DMF (160 mL) were then added to quench the addition reaction, the reaction mixture was allowed to warm up to room temperature and stir for overnight. Water (300 mL) was added carefully to quench the methylation reaction, and the resulting mixture was extracted with CH$_2$Cl$_2$ (3×150 mL). The combined organic layer was washed with water (3×150 mL) and brine (200 mL) and dried over sodium sulfate. After concentrating under reduced pressure, the crude off-white solid was purified by column on silica gel (Ethyl Acetate/hexane=1:4) to give dibromide 8 as a white solid (20.1 g, 72%, m.p. 185-186° C.). $^1$H NMR (400 MHz, CDCl$_3$): δ (ppm) 3.41 (s, 12H, OCH$_3$), 6.04 (d, J=10 Hz, 4H, CH=CH), 6.10 (d, J=10 Hz, 4H, CH=CH), 7.25 (d, J=8.4 Hz, 4H, Ar—H), 7.33 (s, 4H, Ar—H), 7.42 (d, J=8.4 Hz, 4H, Ar—H). $^{13}$C NMR (100 MHz, CDCl$_3$): δ (ppm) 51.97 (OCH$_3$), 74.46, 74.52 (C-OMe), 121.58, 126.03, 127.77, 131.40, 132.98, 133.63, 142.51, 142.66 (Ar). HRMS (Q-TOF ES+) m/z calcd for C$_{26}$H$_{23}$BrO$_4$ (M-2OCH$_3$)$^+$: 601.3215, Found (isotopic pattern): 599.3282, 600.3158, 601.3227, 602.3257, 603.3302. IR (neat): 2948, 1483, 1400, 1270, 1072, 1010, 948, 818, 730 cm$^{-1}$.

Example 5

Preparation of 9

An Example of a Compound of Formula XI: See FIG. 2 for Synthetic Scheme

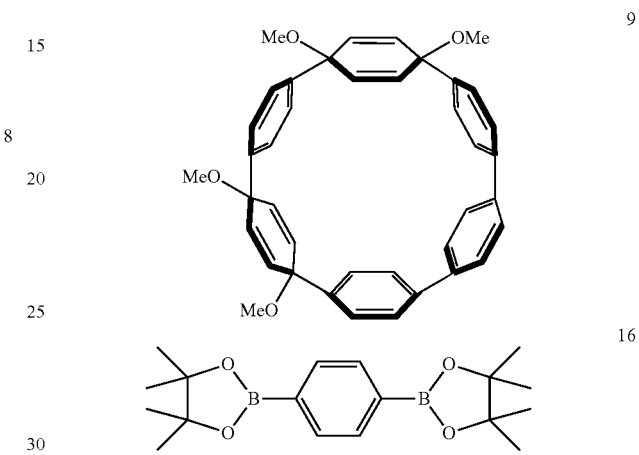

Dibromide 8 (400 mg, 0.6 mmol), 1,4-benzenediboronic acid bis(pinacol) ester (an example of a compound of formula VIII, compound 16) (200 mg, 0.6 mmol), Pd(PPh$_3$)$_4$ (104 mg, 0.09 mmol, 0.15 equiv) and cesium carbonate (Cs$_2$CO$_3$, 977 mg, 3 mmol, 5 equiv) were charged in a 250 mL Schlenk flask under nitrogen, then 110 mL degassed DMF/2-isopropanol (10:1) was added. The result mixture was heated to 120° C. and stirred for 18 h. After cooled down to room temperature, the reaction mixture was transferred to a 500 mL separatory funnel and 100 mL water was added. After extraction with dichloromethane (3×60 mL), the combined organic phase was washed with water (6×50 mL) and dried over sodium sulfate. After removing the solvent under reduced pressure, the crude mixture was purified by silica column chromatography (ethyl acetate/hexane=1:3) to give the [6]macrocycle 9 as a white solid (42 mg, 12%). $^1$H NMR (400 MHz, CDCl$_3$): δ (ppm) 3.30 (s, 6H, OCH$_3$), 3.44 (s, 6H, OCH$_3$), 5.73 (d, J=10, 4H, CH=CH), 6.23 (d, J=10, 4H, CH=CH), 6.78 (s, 4H, Ar—H), 7.22 (d, J=8.4, 4H, Ar—H), 7.33 (d, J=8.4, 4H, Ar—H), 7.47 (s, 4H, Ar—H). $^{13}$C NMR (100 MHz, CDCl$_3$): δ (ppm) 51.16, 52.58 (OCH$_3$), 74.06, 74.14 (C-OMe), 125.60, 126.69, 128.42, 129.02, 132.71, 139.80, 140.13, 141.66, 142.63 (Ar). MALDI-TOF m/z calcd for C$_{40}$H$_{36}$O$_4$ (M)$^+$: 580.71, Found: 581.0. IR (neat): 2954, 1716, 1435, 1257, 1081, 835 cm$^{-1}$. (melting point is not available because compound decomposed when the temperature was raised to 290° C.)

TABLE S1

| Crystal data, data collection and refinement of Compound 9. Compound 9 ([6]macrocycle) | |
|---|---|
| C$_{40}$H$_{36}$O$_4$ | Z = 4 |
| M$_r$ = 580.69 | F(000) = 1232 |
| Triclinic, P-1 | D$_X$ = 1.255 Mg m$^{-3}$ |

TABLE S1-continued

Crystal data, data collection and refinement of Compound 9.
Compound 9 ([6]macrocycle)

| | |
|---|---|
| Hall symbol: -P 1 | Cu Kα radiation, λ, = 1.54178 Å |
| a = 12.7572 (18) Å | Cell parameters from 9523 reflections |
| b = 14.881 (2) Å | θ = 2.7-66.0° |
| c = 17.141 (2) Å | μ = 0.63 mm$^{-1}$ |
| α = 78.434 (6)° | T = 220 K |
| β = 80.758 (5)° | Prism, yellow |
| γ = 76.078 (5)° | 0.23 × 0.11 × 0.05 mm |
| V = 3072.8 (7) Å$^3$ | |
| Bruker Proteum-R diffractometer | 10535 independent reflections |
| Radiation source: rotating anode multilayer | 9327 reflections with l > 2 s(l) Rint = 0.042 |
| w & f scans | qmax = 66.8°, qmin = 2.7° |
| Absorption correction: multi-scan SADABS (Sheldrick, 1997) | h = −15→14 |
| Tmin = 0.642, Tmax = 0.753 | k = −17→17 |
| 72989 measured reflections | l = −20→20 |
| Refinement on F2 | Primary atom site location: structure-invariant direct methods |
| Least-squares matrix: full | Secondary atom site location: difference Fourier map |
| R[F2 > 2 s(F2)] = 0.047 | Hydrogen site location: inferred from neighbouring sites |
| wR(F2) = 0.124 | H-atom parameters constrained |
| S = 1.05 | w = 1/[s2(Fo2) + (0.0602P)2 + 0.8651P] where P = (Fo2 + 2Fc2)/3 (D/s)max = 0.001 |
| 10535 reflections | Dρmax = 0.40 e Å-3 |
| 838 parameters | Dρmin = −0.24 e Å-3 |
| 34 restraints | |

Example 6

Preparation of 1

An Example of a Compound of Formula I: See FIG. 2 for Synthetic Scheme

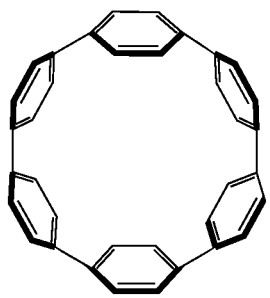

1

To a 10 mL dry roundbottom flask charged with a solution of naphthalene (128 mg, 1 mmol) in 5 mL dry THF was added sodium metal (35 mg, 1.5 mmol) under nitrogen. The reaction mixture was stirred for 18 h at room temperature. After this time, a green solution containing sodium naphthalenide was formed.

In a separate 25 mL dry flask charged with the [6]macrocycle 9 (40 mg, 0.07 mmol), dry THF (6 mL) was added and the resulting solution was cooled down to −78° C. At this point, the sodium naphthalenide (2 mL) prepared above was added. The reaction mixture was stirred for 30 minutes before the addition of iodine (I$_2$, 1 mL of a 1 M in THF). The reaction mixture was warmed up to room temperature and sodium thiosulfate (saturated solution) was added to remove excess I$_2$. Water (10 mL) was then added and the mixture was extracted with dichloromethane (3×10 mL), which was combined and washed brine (30 mL) and dried over sodium sulfate. After removing the solvent under reduced pressure, the crude mixture was loaded onto a preparation TLC plate, and chromatographed with 45% dichloromethane in hexanes. After the purification, the [6]Cycloparaphenylene 1 was received as an orange solid (15 mg, 48%). $^1$H NMR (400 MHz, CDCl$_3$): δ (ppm) 7.64 (s, 24H, Ar—H). $^{13}$C NMR (100 MHz, CDCl$_3$): δ (ppm) 127.03, 134.88. MALDI-TOF m/z calcd for C$_{36}$H$_{24}$ (M)$^+$: 456.58, Found: 457.0. IR (neat): 2955, 2924, 2853, 1261, 813 cm$^{-1}$. (melting point is not available because compound decomposed when the temperature was raised to 350° C.)

TABLE S2

Crystal data, data collection and refinement of [6]CPP.
Compound 1 ([6]cycloparaphenylene)

| | |
|---|---|
| C$_{36}$H$_{24}$ | D$_x$ = 1.126 Mg m$^{-3}$ |
| M$_r$ = 456.55 | Cu Kα radiation, λ, = 1.54178 Å |
| Hexagonal, R-3 | Cell parameters from 9879 reflections |
| Hall symbol: -R 3 | θ = 4.6-65.7° |
| a = 19.3957 (4) Å | μ = 0.48 mm$^{-1}$ |
| c = 6.1998 (2) Å | T = 100 K |
| V = 2019.85 (9) Å$^3$ | Prism, colorless |
| Z = 3 | 0.13 × 0.10 × 0.08 mm |
| F(000) = 720 | |
| Bruker Proteum-R diffractometer | 787 independent reflections |
| Radiation source: rotating anode multilayer | 776 reflections with l > 2 s(l) Rint = 0.0000 |
| f & w scans | qmax = 66.1°, qmin = 4.6° |
| Absorption correction: multi-scan SADABS (Sheldrick, 1997) | h = 0→19 |
| Tmin = 0.697, Tmax = 0.753 | k = 0→19 |
| 787 measured reflections | l = −7→7 |
| Refinement on F2 | Secondary atom site location: difference Fourier map |
| Least-squares matrix: full | Hydrogen site location: inferred from neighbouring sites |
| R[F2 > 2 s(F2)] = 0.051 | H-atom parameters constrained |
| wR(F2) = 0.155 | w = 1/[s2(Fo2) + (0.0978P)2 + 2.7014P] |
| S = 1.11 | where P = (Fo2 + 2Fc2)/3 (D/s)max < 0.001 |
| 787 reflections | Dρmax = 0.33 e Å-3 |
| 56 parameters | Dρmin = −0.24 e Å-3 |
| 0 restraints | Extinction correction: SHELXL, Fc* = kFc[1 + 0.001 × Fc2l3/sin(2q)]−1/4 |
| Primary atom site location: structure-invariant direct methods | Extinction coefficient: 0.0019 (7) |

Example 7

Preparation of 10

Figure 3:
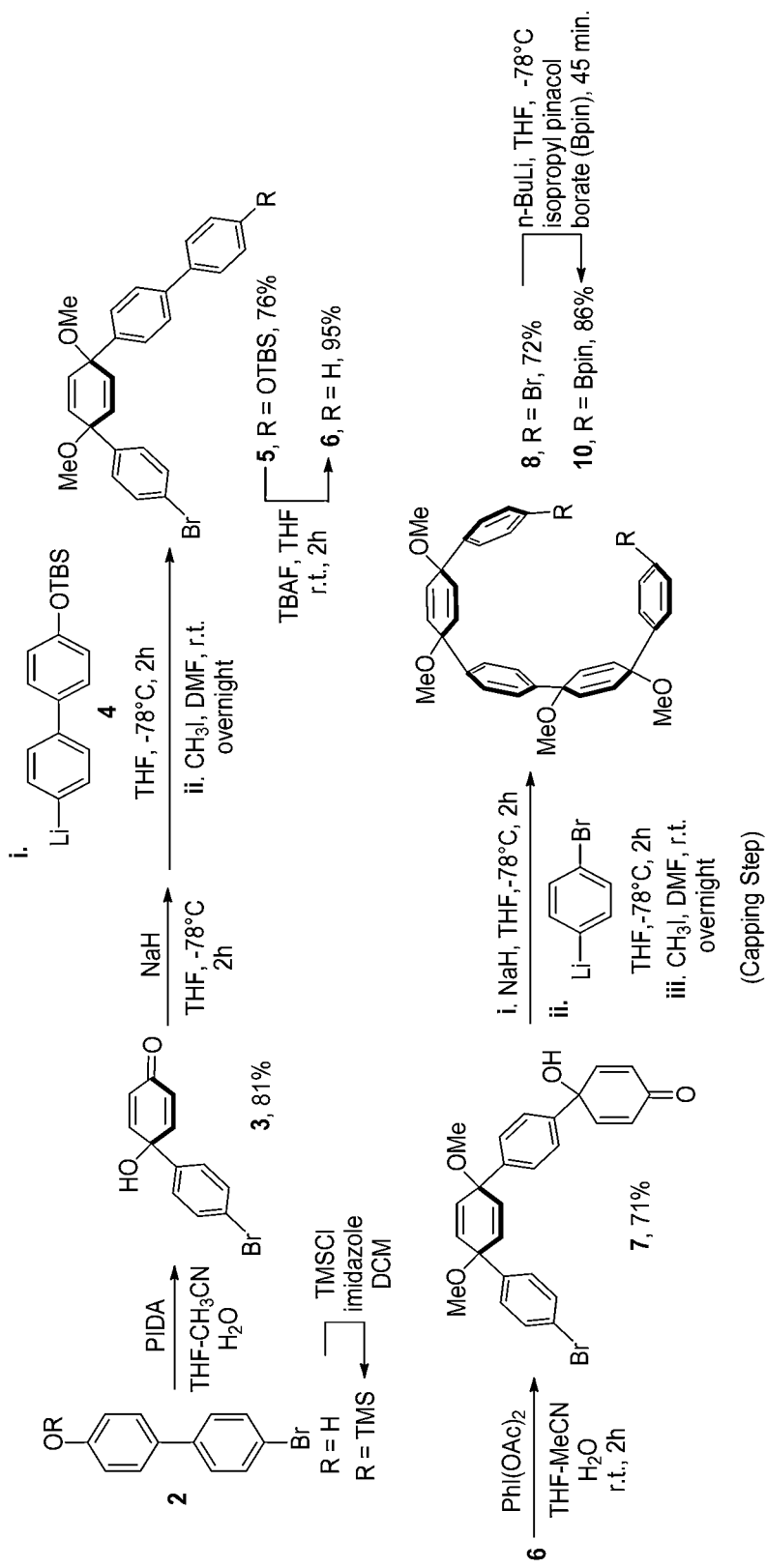
FIG. 3 is a synthetic scheme for the synthesis of [n]CPP intermediates (i.e. [n]macrocycle precursors) that can optionally be used in 2-piece assembly.

An Example of a Compound of Formula VIII: See FIG. 3 for Synthetic Scheme

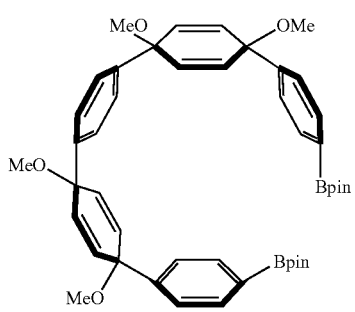

Dibromide 8 (10 g, 15 mmol) was dissolved in 240 mL of tetrahydrofuran and cooled down to −78° C. To this solution was added n-BuLi (13.2 mL, 33 mmol, 2.5 M in hexane) over 6 min. After the addition of n-BuLi, neat isopropyl pinacol borate (11.84 mL, 60 mmol) was added immediately and rapidly, and the solution was stirred for 30 min at −78° C. The reaction was then warmed up to room temperature and water (100 mL) was added to the solution and the mixture was allowed to stir for 15 min before extracting with $CH_2Cl_2$ (3×80 mL). The combined organic layers were washed with a saturated brine solution and then dried over magnesium sulfate. After removing the solvent under vacuum, the crude product was purified by recrystallization from hot ethyl acetate to afford compound 10 as a white solid (9.8 g, 86%, m.p. 251° C.). $^1$H NMR (400 MHz, $CDCl_3$): δ (ppm) 1.33 (s, 24H, $CH_3$), 3.42 (d, J=3.6 Hz, 12H, $OCH_3$), 6.08 (s, 8H, CH=CH), 7.34 (s, 4H, Ar), 7.39 (d, J=8.4 Hz, 4H, Ar—H), 7.74 (d, J=8.4 Hz, 4H, Ar—H). $^{13}$C NMR (100 MHz, $CDCl_3$): δ (ppm) 24.84 ($CH_3$), 51.92 ($OCH_3$), 74.61, 74.90 (C-OMe), 83.73 ($C(Me)_2$), 125.27, 126.05, 133.16, 133.35, 134.90, 142.70, 146.43 (Ar). HRMS (Q-TOF ES+) m/z calcd for $C_{46}H_{56}B_2O_8Na$ (M+Na)$^+$: 781.4075. Found: 781.4054. IR (neat): 2979, 2933, 2823, 1606, 1397, 1361, 1324, 1268, 1143, 1090, 1075, 1011, 947, 835 cm$^{-1}$.

It is to be understood that this synthetic procedure can be used to generate isopropyl pinacol diboronates of various (i.e. ring lengths) sizes using dibromides of different size.

Example 8

Preparation of 11

An Example of a Compound of Formula XI; See FIG. 5 for 2-Piece Assembly

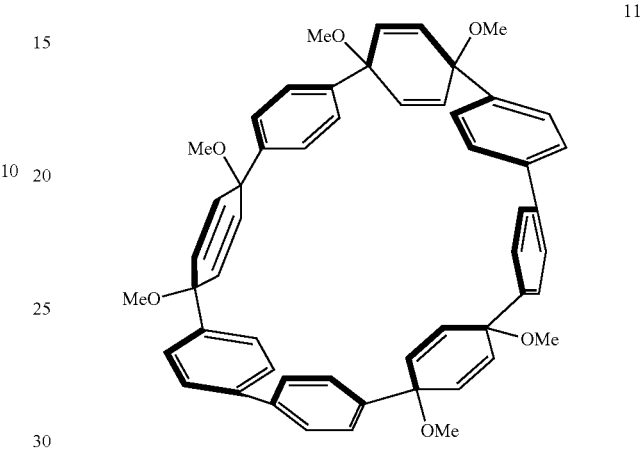

Dibromide 8 (3.0 g, 4.5 mmol), diboronate 12 (2.45 g, 4.5 mmol), $Pd(OAc)_2$ (303 mg, 0.45 mmol, 0.1 equiv) and $Cs_2CO_3$ (7.33 g, 45 mmol, 5 equiv) were charged in a 2 L flask under nitrogen, then 1650 mL degassed DMF/2-isopropanol (10:1) was added.

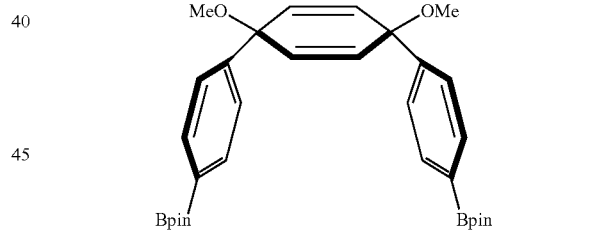

The result mixture was heated to 100° C. and stirred for 24 h. After cooling to room temperature (rt), the mixture was filtered through a short plug of Celite, and 500 mL water was added to the filtrate. After extraction with dichloromethane (3×150 mL), the combined organic phase was washed with water (8×100 mL) and dried over sodium sulfate. After removing the solvent under vacuum, the crude mixture was purified by silica column chromatography (ethyl acetate/hexane=2:3) to give the [8]macrocycle 11 as a white solid (1.8 g, 50%). $^1$H NMR (400 MHz, $CDCl_3$): δ (ppm) 3.40-3.48 (m, 18H, $OCH_3$), 6.06 (d, J=10.4 Hz, 4H, CH=CH), 6.14 (d, J=10.4 Hz, 4H, CH=CH), 6.26 (s, 4H, CH=CH), 7.13 (J=8.4 Hz, 4H, Ar—H), 7.37 (J=8.4 Hz, 4H, Ar—H), 7.50-7.53 (m, 12H, Ar). $^{13}$C NMR (100 MHz, $CDCl_3$): δ (ppm) 51.81, 52.12, 52.14 ($OCH_3$), 74.02, 74.54, 75.91 (C-OMe), 126.23, 126.51, 126.82, 127.15, 132.78, 133.50, 139.66, 139.85, 140.49, 142.80, 143.32 (Ar). MALDI-TOF m/z calcd for $C_{54}H_{50}O_6$ (M)$^+$: 794.97, Found: 795.0. IR (neat): 3030, 2980, 2929, 2893, 2818, 1606, 1493, 1447, 1392, 1358, 1265, 1224, 1172, 1074, 1014, 948, 821 cm$^{-1}$. (melting point is not available because compound decomposed when the temperature was raised to 280° C.).

It is to be understood that compound 11 can then be converted to [8]cycloparaphenylene using the procedure as substantially described in Example 6—See also Example 10).

It is also to be understood that this general procedure can be used to produce [n]macrocycles of various size, wherein the actual size [n] depends on the number of rings in the starting isopropyl pinacol diboronate (e.g. compound 12 has 3 rings) and the number of rings in the dibromide (e.g. compound 8 has 5 rings; 3+5=8 rings; See FIG. 5).

Example 9

Preparation of 13

An Example of a Compound of Formula XI; See FIG. 5 for 2-Piece Assembly

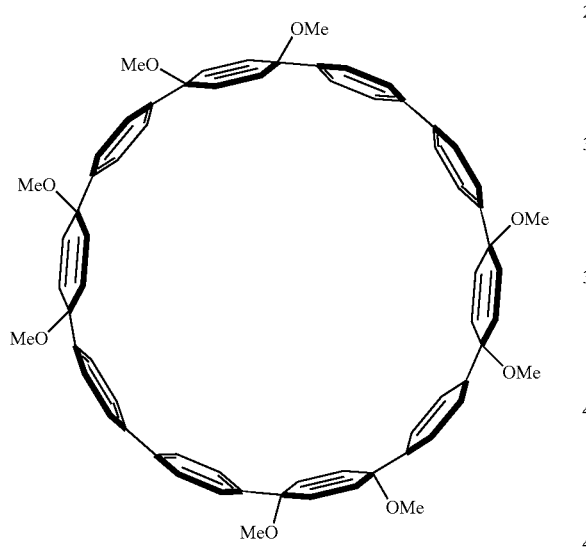

13

Method A:

A mixture of dibromide 8 (664 mg, 1 mmol), diboronate 10 (759 mg, 1 mmol), Pd(OAc)$_2$ (135 mg, 0.2 mmol, 0.2 equiv), S-Phos (82 mg, 0.2 mmol, 0.2 equiv) and potassium phosphate (K$_3$PO$_4$, 849 mg, 4 mmol, 4 equiv) in DMF/H$_2$O (200 mL/20 mL, 10:1) was stirred at 100° C. for 16 h under nitrogen. After cooling down to rt, the mixture was filtered through a short plug of Celite, and 150 mL water was added to the filtrate. After extraction with dichloromethane (3×60 mL), the combined organic phase was washed with water (8×60 mL) and dried over sodium sulfate. After removing the solvent under vacuum, the crude mixture was purified by silica column chromatography (ethyl acetate/hexane=2:3) to give the [10]macrocycle 13 as a white solid (556 mg, 55%). $^1$H NMR (400 MHz, CDCl$_3$): δ (ppm) 3.26 (s, 12H, OCH$_3$), 3.46 (s, 12H, OCH$_3$), 5.73 (d, J=10 Hz, 8H, CH=CH), 5.99 (s, 8H, CH=CH), 6.58 (d, J=10.4 Hz, 8H, Ar), 7.43-7.48 (m, 16H, Ar). $^{13}$C NMR (100 MHz, CDCl$_3$): δ (ppm) 51.26, 52.65 (OCH$_3$), 73.65, 74.93 (C-OMe), 125.07, 127.47, 128.89, 133.74, 133.92, 140.00, 141.28, 141.66 (Ar). MALDI-TOF m/z calcd for C$_{68}$H$_{64}$O$_8$ (M)$^+$: 1009.23, Found: 1009.2. IR (neat): 2920, 2847, 2820, 1739, 1593, 1486, 1449, 1402, 1183, 1074, 1014, 953, 823 cm$^{-1}$. (melting point is not available because compound decomposed when the temperature was raised to 300° C.)

Method B.

Dibromide 8 (3.19 g, 4.8 mmol), diboronate 10 (3.64 g, 4.8 mmol), Pd(OAc)$_2$ (324 mg, 0.48 mmol, 0.1 equiv) and Cs$_2$CO$_3$ (7.82 g, 48 mmol, 5 equiv) were charged in a 2 L flask under nitrogen, then the degassed DMF (1600 mL) and 2-isopropanol (160 mL) was added. The result mixture was heated to 100° C. and stirred for 24 h. After cooling down to rt, the mixture was filtered through a short plug of Celite, and 500 mL water was added to the filtrate. After extraction with dichloromethane (3×150 mL), the combined organic phase was washed with water (8×100 mL) and dried over sodium sulfate. After removing the solvent under vacuum, the crude mixture was purified by silica column chromatography (ethyl acetate/hexane=2:3) to give the [10]macrocycle 13 as a white solid (2.15 g, 44%).

Example 10

Preparation of 14

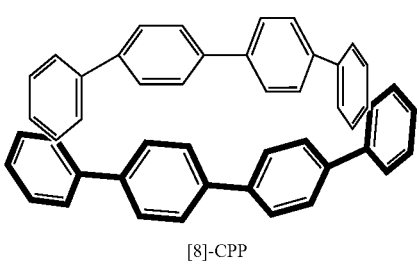

14

[8]-CPP

To a 50 mL dry roundbottom flask charged with a solution of naphthalene (3.85 g, 30 mmol) in 30 mL dry THF was added sodium metal (1.04 g, 45 mmol) under nitrogen. The reaction mixture was stirred for 18 h at room temperature. After this time, a green solution containing sodium naphthalenide (1.0 M in THF) was formed.

[8]macrocycle 11 (1.8 g, 2.26 mmol) was dissolved in 160 mL THF under nitrogen and cooled down to −78° C. At this point, the freshly prepared sodium naphthalenide (18 mL, 18 mmol, 1.0 M in THF (see above)) was added. The reaction mixture was stirred for 2 h at −78° C. before the addition of I$_2$ (15 mL of a 1 M solution in THF). The resulting mixture was then warmed up to room temperature and sodium thiosulfate (saturated solution) was carefully added to remove excess I$_2$. Water (60 mL) was then added and the mixture was extracted with dichloromethane (3×60 mL), which was combined and washed with brine (60 mL) and dried over sodium sulfate. After removing the solvent under reduced pressure, the crude yellow solid was purified by column on silica gel (CH$_2$Cl$_2$/Hexanes=1:1) to give [8]-Cycloparaphenylene 14 as a yellow solid (1.04 g, 75%). $^1$H NMR (400 MHz, CDCl$_3$): δ (ppm) 7.48 (s, 32H). $^{13}$C NMR (100 MHz, CDCl$_3$): δ (ppm) 127.44, 137.63. MALDI-TOF m/z calculated for C$_{48}$H$_{32}$ (M)$^+$: 608.25, Found: 608.4.

TABLE S3

Crystal data, data collection and refinement of [8]CPP (14).
Compound 14 ([8]CPP)

| | |
|---|---|
| $C_{48}H_{32}$ | $V = 1934.66 (5)$ Å$^3$ |
| $M_r = 608.74$ | $Z = 2$ |
| Monoclinic, $P2_1/n$ | Cu K$\alpha$ radiation, $\lambda$, = 1.54178 Å |
| $a = 12.9325 (2)$ Å | $\mu = 0.45$ mm$^{-1}$ |
| $b = 8.0103 (1)$ Å | $T = 100$ K |
| $c = 19.3676 (3)$ Å | $0.15 \times 0.09 \times 0.09$ mm |
| $\beta = 105.363 (1)°$ | Block, yellow |
| $\theta = 3.7$-$65.7°$ | $D_x = 1.045$ Mg m$^{-3}$ |
| Bruker Proteum-R diffractometer | 3374 independent reflections |
| Absorption correction: multi-scan SADABS (Sheldrick, 1997) | 3192 reflections with $I > 2 s(l)$ |
| Tmin = 0.657, Tmax = 0.753 | Rint = 0.0000 |
| 3374 measured reflections | $h = -15 \rightarrow 10$ |
| | $k = 0 \rightarrow 9$ |
| | $l = -10 \rightarrow 22$ |
| $R[F^2 > 2\sigma(F^2)] = 0.041$ | 0 restraints |
| $wR(F^2) = 0.113$ | H atoms treated by a mixture of independent and constrained refinement |
| $S = 1.09$ | $\Delta\rangle_{max} = 0.22$ e Å$^{-3}$ |
| 3374 reflections | $\Delta\rangle_{min} = -0.16$ e Å$^{-3}$ |
| 220 parameters | |

TABLE S4

Crystal data, data collection and refinement of [10]CPP(15).
Compound 15 ([10]CPP)

| | |
|---|---|
| $C_{60}H_{40}$ | $V = 2544.84 (12)$ Å$^3$ |
| $M_r = 760.92$ | $Z = 2$ |
| Monoclinic, $P2_1/c$ | Cu K$\alpha$ radiation, $\lambda$, = 1.54178 Å |
| $a = 15.9075 (4)$ Å | $\mu = 0.43$ mm$^{-1}$ |
| $b = 8.1405 (2)$ Å | $T = 100$ K |
| $c = 20.7418 (6)$ Å | $0.08 \times 0.07 \times 0.06$ mm |
| $\beta = 108.655 (2)°$ | $D_x = 0.993$ Mg m$^{-3}$ |
| Block, yellow | $\theta = 2.9$-$65.7°$ |
| Bruker Proteum-R diffractometer | 4384 independent reflections |
| Absorption correction: multi-scan SADABS (Sheldrick, 1997) | 3596 reflections with $I > 2\sigma(l)$ |
| $T_{min} = 0.684, T_{max} = 0.753$ | $R_{int} = 0.040$ |
| | $h = -18 \rightarrow 17$ |
| 4384 measured reflections | $k = 0 \rightarrow 9$ |
| | $l = 0 \rightarrow 24$ |
| $R[F^2 > 2\sigma(F^2)] = 0.051$ | 0 restraints |
| $wR(F2) = 0.146$ | H-atom parameters constrained $w = 1/[\sigma^2(F_o^2) + (0.0964P)^2 + 0.2599P]$ where $P = (F_o^2 + 2F_c^2)/3$ |
| $S = 1.10$ | $\Delta\rangle_{max} = 0.42$ e Å$^{-3}$ |
| 4384 reflections | $\Delta\rangle_{min} = -0.19$ e Å$^{-3}$ |
| 271 parameters | $(\Delta/\sigma)_{max} < 0.001$ |

Example 11

Preparation of 15

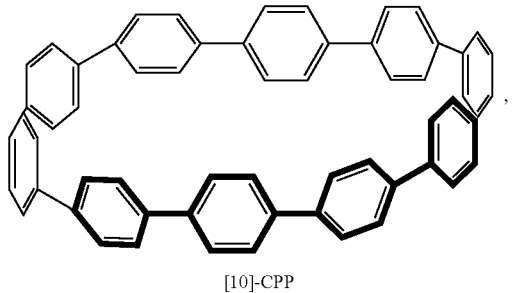

[10]-CPP

[10]macrocycle 13 (2.1 g, 2.08 mmol) was dissolved in 160 mL THF under nitrogen and cooled down to −78° C. At this point, the freshly prepared sodium naphtalenide (25 mL, 25 mmol, 1.0 M in THF (see above)) was added. The reaction mixture was stirred for 2 h at −78° C. before the addition of I$_2$ (15 mL of a 1 M solution in THF). The resulting mixture was then warmed up to room temperature and sodium thiosulfate (saturated solution) was carefully added to remove excess I$_2$. Water (60 mL) was then added and the mixture was extracted with dichloromethane (3×60 mL), which was combined and washed with brine (60 mL) and dried over sodium sulfate. After removing the solvent under reduced pressure, the crude yellow solid was purified by column on silica gel (CH$_2$Cl$_2$/Hexanes=1:1) to give [10]Cycloparaphenylene 15 as a yellow solid (1.03 g, 65%). $^1$H NMR (400 MHz, CDCl$_3$): $\delta$ (ppm) 7.56 (s, 32H). $^{13}$C NMR (100 MHz, CDCl$_3$): $\delta$ (ppm) 127.34, 138.14. MALDI-TOF m/z calculated for $C_{60}H_{40}$ (M)$^+$: 760.31. Found: 760.5.

REFERENCES

US Patent and Published Patent Applications

1. Jasti et al., U.S. patent application Ser. No. 12/955,211.

Scientific Publications

1. Jasti et al., *J. Am. Chem. Soc.* 2008, 130, 17646-17647.
2. Guha et al., *J. Indian Chem. Soc.* 1934, 11, 95-100.
3. Vögtle et al., *Chem. Ber.* 1993, 126, 1723-1732.
4. Itami et al., *Angew. Chem.* 2009, 121, 6228-6232; *Angew. Chem. Int. Ed.* 2009, 48, 6112-6116.
5. Yamago et al., *Angew. Chem.* 2010, 122, 769-771; *Angew. Chem. Int. Ed.* 2010, 49, 757-759.
6. Itami et al., *Angew. Chem.* 2010, 122, 10400-10403; *Angew. Chem. Int. Ed.* 2010, 49, 10202-10205.
7. Yamago et al., *J. Am. Chem. Soc.* 2011, 133, 8354-8361.
8. Itami et al., *Angew. Chem.* 2011, 123, 3302-3306; *Angew. Chem. Int. Ed.* 2011, 50, 3244-3248.
9. Itami et al., *Chem. Lett.* 2011, 40, 423-425.
10. Itami et al., *Org. Lett.* 2011, 13, 2480-2483.
11. S. Hitosugi et al., *Nat. Commun.* 2011, 2, 1505.
12. Jasti et al., *J. Am. Chem. Soc.* 2011, 133, 15800-15802.
13. Jasti et al., *Angew. Chem.* 2012, 124, 2524-2526; *Angew. Chem. Int. Ed.* 2012, 51, 2474-2476.
14. Itami et al., *Org. Lett.* 2012, ASAP.
15. Jasti et al., *Chem. Phys. Lett.* 2010, 494, 1-7.
16. Scott et al., *J. Mater. Chem.* 2011, 21, 1373-1381.
17. Scott et al., *J. Am. Chem. Soc.* 2009, 131, 16006-16007.
18. Scott et al., *Angew. Chem.* 2010, 122, 6776-6778; *Angew. Chem. Int. Ed.* 2010, 49, 6626-6628.
19. Kizek et al., *J. Mater. Chem.* 2011, 21, 15872-15884.
20. Tour et al., *J. Am. Chem. Soc.* 2006, 128, 15824-15829.
21. Morokuma et al., *ChemPhysChem* 2012, Early View.
22. Pichierri et al., *Phys. Chem. Chem. Phys.* 2010, 12, 2751-2757.
23. Wong, *J. Phys Chem. C* 2009, 113, 21921-21927.
24. Itami et al., *Org. Biomol. Chem.* 2012, 10, (DOI:10.1039/C2OB25199J).

24. Yamago et al., *Angew. Chem.* 2011, 123, 8492-8494; *Angew. Chem. Int. Ed.* 2011, 50, 8342-8344.
26. Varghese et al., *Eur. J. Org. Chem.* 2003, 660-665.
27. Kurata et al., *Chem. Rev.* 2006, 106, 5250-5273.
28. Hirsch et al., *Angew. Chem.* 2004, 116, 2380-2383; *Angew. Chem. Int. Ed.* 2004, 43, 2326-2329.
29. Aida et al., *Chem. Soc. Rev.* 2007, 36, 189-197.
30. Martin et al., *Chem. Soc. Rev.* 2008, 37, 1512-1519.
31. Olmstead et al., *J. Am. Chem. Soc.* 2007, 129, 3842-3843.
32. Luzzi et al., *Nature* 1998, 396, 323-324.
33. Yazdani et al., *Science,* 2002, 295, 828-831.

While the present teachings are described in conjunction with various embodiments, it is not intended that the present teachings be limited to such embodiments. On the contrary, the present teachings encompass various alternatives, modifications and equivalents, as will be appreciated by those of skill in the art. Thus, the invention as contemplated by applicants extends to all functionally equivalent structures, methods and uses, such as are within the scope of the appended claims.

Moreover, in the following claims it should be understood that the order of steps or order for performing certain actions (e.g. mixing of reactants) is immaterial so long as the present teachings remain operable. Unless expressly stated otherwise or where performing the steps of a claim in a certain order would be non-operative, the steps and/or substeps of the following claims can be executed in any order. Moreover, two or more steps or actions can be conducted simultaneously.

We claim:

1. A composition comprising at least two molecules of cycloparaphenylene.

2. The composition of claim 1, wherein the composition is electrically and/or thermally conductive.

3. The composition of claim 1, wherein the [6]cycloparaphenylene molecules self-assemble to form nanotubes.

4. The composition of claim 3, wherein the nanotubes are uniform in size or substantially uniform in size.

5. The composition of claim 3, wherein the nanotubes are straight or substantially straight.

6. The composition of claim 3, wherein the nanotubes self-assemble to form a matrix comprising nanopores.

7. The composition of claim 6, wherein the nanopores of the matrix are uniform in diameter or substantially uniform in diameter.

* * * * *